United States Patent
Simpson et al.

(10) Patent No.: US 12,039,585 B2
(45) Date of Patent: Jul. 16, 2024

(54) SYSTEM AND METHOD FOR BLOOD AND SALIVA OPTIMIZED FOOD CONSUMPTION AND DELIVERY

(71) Applicant: CirclesX LLC, Houston, TX (US)

(72) Inventors: Erik M Simpson, Houston, TX (US); Gavin Simpson, Houston, TX (US)

(73) Assignee: CIRCLESX LLC, Houston, TX (US)

( * ) Notice: Subject to any disclaimer, the term of this patent is extended or adjusted under 35 U.S.C. 154(b) by 974 days.

(21) Appl. No.: 15/484,059

(22) Filed: Apr. 10, 2017

(65) Prior Publication Data
US 2018/0293638 A1 Oct. 11, 2018

(51) Int. Cl.
| | | |
|---|---|---|
| G06Q 30/0601 | (2023.01) | |
| G01N 33/487 | (2006.01) | |
| G01N 33/49 | (2006.01) | |
| G06N 3/042 | (2023.01) | |
| G06N 3/045 | (2023.01) | |
| G06N 3/08 | (2023.01) | |
| G16B 40/00 | (2019.01) | |
| G16H 20/60 | (2018.01) | |

(52) U.S. Cl.
CPC ... *G06Q 30/0631* (2013.01); *G01N 33/48792* (2013.01); *G01N 33/492* (2013.01); *G06N 3/042* (2023.01); *G06N 3/08* (2013.01); *G06Q 30/0633* (2013.01); *G16B 40/00* (2019.02); *G16H 20/60* (2018.01); *G06N 3/045* (2023.01)

(58) Field of Classification Search
None
See application file for complete search history.

(56) References Cited

U.S. PATENT DOCUMENTS

| | | |
|---|---|---|
| D209,710 S | 12/1967 | Bruce |
| 4,476,954 A | 10/1984 | Johnson et al. |
| D318,073 S | 7/1991 | Jang |
| 5,412,560 A | 5/1995 | Dennison |
| 5,604,676 A | 2/1997 | Penzias |
| 5,726,885 A | 3/1998 | Klein et al. |
| 5,751,245 A | 3/1998 | Klein et al. |
| 5,973,619 A | 10/1999 | Paredes |
| 6,175,831 B1 | 1/2001 | Weinreich et al. |
| 6,240,396 B1 | 5/2001 | Walker et al. |
| 6,285,999 B1 | 9/2001 | Page |
| D453,945 S | 2/2002 | Shan |
| 6,356,838 B1 | 3/2002 | Paul |
| D460,952 S | 7/2002 | Kataoka |
| 6,421,606 B1 | 7/2002 | Asai et al. |
| 6,434,530 B1 | 8/2002 | Sloane et al. |
| D468,738 S | 1/2003 | Lin |
| D469,089 S | 1/2003 | Lin |
| 6,609,103 B1 | 8/2003 | Kolls |
| 6,618,062 B1 | 9/2003 | Brown et al. |
| 6,646,659 B1 | 11/2003 | Brown et al. |
| 6,663,564 B2 | 12/2003 | Miller-Kovach et al. |
| 6,708,879 B2 | 3/2004 | Hunt |
| 6,850,907 B2 | 2/2005 | Lutnick et al. |
| 7,090,638 B2 | 8/2006 | Vidgen |
| 7,373,320 B1 | 5/2008 | Mcdonough |
| D590,396 S | 4/2009 | Lo |
| 7,584,123 B1 | 9/2009 | Karonis et al. |
| 7,634,442 B2 | 12/2009 | Alvarado et al. |
| 7,680,690 B1 | 3/2010 | Catalano |
| 7,680,770 B1 | 3/2010 | Buyukkokten et al. |
| 7,711,629 B2 | 5/2010 | Laurent et al. |
| 7,747,739 B2 | 6/2010 | Bridges et al. |
| 7,756,633 B2 | 7/2010 | Huang et al. |
| 7,788,207 B2 | 8/2010 | Alcorn et al. |
| D628,171 S | 11/2010 | Hakopian |
| 7,886,166 B2 | 2/2011 | Shnekendorf et al. |
| D638,879 S | 5/2011 | Suto |
| 7,987,110 B2 | 7/2011 | Cases et al. |
| 8,024,234 B1 | 9/2011 | Thomas et al. |

(Continued)

FOREIGN PATENT DOCUMENTS

| | | |
|---|---|---|
| CN | 107341968 A | 11/2017 |
| GB | 2539556 A | 12/2016 |

(Continued)

OTHER PUBLICATIONS

Netlingo, https://web.archive.org/web/20170122184857/https://www.netlingo.com/word/electronic-exchange.php, dated Oct. 22, 2017, 1 page.
Laseter, Tim, "B2B benchmark: The State of Electronic Exchanges", Tech & Innovation, dated Oct. 1, 2001, 25 pages.
Directed Graph, https://en.wikipedia.org/wiki/Directed_graph, pp. 1-6, 2022.
About IBM Food Trust, https://www.ibm.com/downloads/cas/E9DBNDJG, pp. 1-17, 2019.
IBM Blockchain Transparent Supply, https://www.ibm.com/downloads/cas/BKQDK0M2, pp. 1-14, Aug. 2020.
Radocchia, Samantha, 3 Innovative Ways Blockchain Will Build Trust in the Food Industry, https://www.forbes.com/sites/samantharadocchia/2018/04/26/3-innovative-ways-blockchain-will-build-trust-in-the-food-industry/?sh=65bc79f42afc, Forbes, pp. 1-5, Apr. 26, 2018.

(Continued)

*Primary Examiner* — Lori A. Clow
(74) *Attorney, Agent, or Firm* — Pramudji Law Group PLLC; Ari Pramudji

(57) ABSTRACT

A computer implemented method for use in conjunction with a computing device, system, network, and cloud with touch screen two dimension display or augmented/mixed reality three dimension display comprising: obtaining, analyzing and detecting user blood and saliva chemistry data and mapping the blood and saliva data into a database associated with a specific user, applying the data with optimization equations and mapping equations to food chemistry such that a user may order food and beverage from a food/beverage distribution point or have food/beverage delivered to the user which has been specifically optimized for their specific blood characteristic target ranges. The method and system uses recursive techniques and neural networks to learn how to optimize food and beverage nutrient efficiency into the users blood chemistry.

18 Claims, 34 Drawing Sheets

(56) References Cited

U.S. PATENT DOCUMENTS

| | | |
|---|---|---|
| 8,065,191 B2 | 11/2011 | Senior |
| D650,385 S | 12/2011 | Chiu |
| 8,121,780 B2 | 2/2012 | Gerdes et al. |
| 8,249,946 B2 | 8/2012 | Froseth et al. |
| 8,296,335 B2 | 10/2012 | Bouve et al. |
| 8,388,451 B2 | 3/2013 | Auterio et al. |
| 8,570,244 B2 | 10/2013 | Mukawa |
| 8,762,035 B2 | 6/2014 | Levine et al. |
| 8,798,593 B2 | 8/2014 | Brown et al. |
| 8,918,411 B1 | 12/2014 | Latif et al. |
| 8,920,175 B2 | 12/2014 | Black et al. |
| 8,930,490 B2 | 1/2015 | Brown et al. |
| 8,968,099 B1 | 3/2015 | Hanke et al. |
| 9,011,153 B2 * | 4/2015 | Bennett .................. G16H 20/30 434/127 |
| 9,020,763 B2 | 4/2015 | Faaborg et al. |
| 9,077,204 B2 | 7/2015 | More et al. |
| 9,092,826 B2 | 7/2015 | Deng et al. |
| 9,159,088 B2 * | 10/2015 | Dillahunt .......... G06Q 30/0261 |
| 9,213,957 B2 | 12/2015 | Stefik et al. |
| 9,274,540 B2 | 3/2016 | Anglin et al. |
| 9,292,764 B2 | 3/2016 | Yun et al. |
| 9,387,928 B1 | 7/2016 | Gentry et al. |
| 9,389,090 B1 | 7/2016 | Levine et al. |
| 9,389,094 B2 | 7/2016 | Brenner et al. |
| 9,410,963 B2 | 8/2016 | Martin et al. |
| 9,436,923 B1 | 9/2016 | Sriram et al. |
| D772,828 S | 11/2016 | Kusumoto |
| 9,528,972 B2 | 12/2016 | Minvielle |
| 9,558,515 B2 | 1/2017 | Babu et al. |
| 9,665,983 B2 | 5/2017 | Spivack |
| 9,880,577 B2 | 1/2018 | Dyess et al. |
| 9,952,042 B2 | 4/2018 | Abovitz et al. |
| 9,960,637 B2 | 5/2018 | Sanders et al. |
| 9,978,282 B2 | 5/2018 | Lambert et al. |
| D832,355 S | 10/2018 | Castro |
| 10,262,289 B2 * | 4/2019 | Vaananen .......... G06Q 20/3224 |
| 10,395,332 B1 | 8/2019 | Konrardy et al. |
| 10,403,050 B1 | 9/2019 | Beall et al. |
| 10,460,520 B2 | 10/2019 | Simpson et al. |
| 10,533,850 B2 | 1/2020 | Abovitz et al. |
| 10,586,084 B2 | 3/2020 | Burch et al. |
| 10,685,503 B2 | 6/2020 | Ricci |
| 10,737,585 B2 | 8/2020 | Chaudhary et al. |
| D896,315 S | 9/2020 | Castro |
| 10,832,337 B1 | 11/2020 | Floyd et al. |
| 10,872,381 B1 | 12/2020 | Leise et al. |
| D910,758 S | 2/2021 | Leong |
| 11,138,827 B2 | 10/2021 | Simpson |
| D938,375 S | 12/2021 | Zhang |
| 11,288,563 B2 | 3/2022 | Lee et al. |
| 11,296,897 B2 | 4/2022 | Endress et al. |
| 11,298,017 B2 | 4/2022 | Tran |
| 11,298,591 B2 | 4/2022 | Evancha |
| 11,555,709 B2 | 1/2023 | Simpson |
| 11,586,993 B2 | 2/2023 | Handler et al. |
| D980,210 S | 3/2023 | Wu |
| D993,316 S | 7/2023 | Lin |
| D1,000,137 S | 10/2023 | Shuster |
| D1,007,451 S | 12/2023 | Im |
| D1,024,065 S | 4/2024 | Kim |
| 2002/0004788 A1 | 1/2002 | Gros et al. |
| 2002/0013718 A1 | 1/2002 | Cornwell |
| 2002/0013761 A1 | 1/2002 | Bundy |
| 2002/0017997 A1 | 2/2002 | Wall |
| 2002/0065738 A1 | 5/2002 | Riggs et al. |
| 2002/0065766 A1 | 5/2002 | Brown et al. |
| 2002/0133456 A1 | 9/2002 | Lancaster et al. |
| 2002/0161689 A1 | 10/2002 | Segal |
| 2003/0055776 A1 | 3/2003 | Samuelson |
| 2003/0191725 A1 | 10/2003 | Ratliff et al. |
| 2003/0233311 A1 | 12/2003 | Bramnick et al. |
| 2004/0019552 A1 | 1/2004 | Tobin |
| 2004/0115596 A1 | 6/2004 | Snyder et al. |
| 2004/0249742 A1 | 12/2004 | Laurent et al. |
| 2004/0260581 A1 | 12/2004 | Baranowski et al. |
| 2005/0021346 A1 | 1/2005 | Nadan et al. |
| 2005/0027637 A1 | 2/2005 | Kohler |
| 2005/0132070 A1 | 6/2005 | Redlich et al. |
| 2005/0288974 A1 | 12/2005 | Baranowski et al. |
| 2005/0288986 A1 | 12/2005 | Barts et al. |
| 2006/0104224 A1 | 5/2006 | Singh |
| 2007/0005224 A1 | 1/2007 | Sutardja |
| 2008/0033833 A1 | 2/2008 | Senior |
| 2008/0040232 A1 | 2/2008 | Perchthaler |
| 2008/0077309 A1 | 3/2008 | Cobbold |
| 2008/0129490 A1 | 6/2008 | Linville et al. |
| 2008/0140557 A1 | 6/2008 | Bowlby et al. |
| 2008/0157990 A1 | 7/2008 | Belzer et al. |
| 2008/0195432 A1 | 8/2008 | Fell et al. |
| 2008/0262892 A1 | 10/2008 | Prager et al. |
| 2009/0221338 A1 | 9/2009 | Stewart |
| 2009/0231687 A1 | 9/2009 | Yamamoto |
| 2009/0271236 A1 | 10/2009 | Ye et al. |
| 2009/0275002 A1 | 11/2009 | Hoggle |
| 2009/0276154 A1 | 11/2009 | Subramanian et al. |
| 2009/0287401 A1 | 11/2009 | Levine et al. |
| 2010/0042421 A1 | 2/2010 | Bai et al. |
| 2010/0081548 A1 | 4/2010 | Labedz |
| 2010/0114790 A1 | 5/2010 | Strimling et al. |
| 2010/0191834 A1 | 7/2010 | Zampiello |
| 2010/0211441 A1 | 8/2010 | Sprigg et al. |
| 2010/0217680 A1 | 8/2010 | Fusz et al. |
| 2010/0228574 A1 | 9/2010 | Mundinger et al. |
| 2010/0280748 A1 | 11/2010 | Mundinger et al. |
| 2010/0280884 A1 | 11/2010 | Levine et al. |
| 2010/0306078 A1 | 12/2010 | Hwang |
| 2011/0025267 A1 | 2/2011 | Kamen et al. |
| 2011/0059693 A1 | 3/2011 | O'Sullivan |
| 2011/0098056 A1 | 4/2011 | Rhoads et al. |
| 2011/0106660 A1 | 5/2011 | Ajjarapu et al. |
| 2011/0202418 A1 | 8/2011 | Kempton et al. |
| 2012/0023032 A1 | 1/2012 | Visdomini |
| 2012/0075067 A1 | 3/2012 | Attaluri |
| 2012/0078743 A1 | 3/2012 | Betancourt |
| 2012/0101629 A1 | 4/2012 | Olsen et al. |
| 2012/0158762 A1 | 6/2012 | IwuchukWu |
| 2012/0303259 A1 | 11/2012 | Prosser |
| 2012/0323645 A1 | 12/2012 | Spiegel et al. |
| 2013/0024041 A1 | 1/2013 | Golden et al. |
| 2013/0035973 A1 | 2/2013 | Desai et al. |
| 2013/0147820 A1 | 6/2013 | Kalai et al. |
| 2013/0173326 A1 | 7/2013 | Anglin et al. |
| 2013/0179205 A1 | 7/2013 | Slinin |
| 2013/0191237 A1 | 7/2013 | Tenorio |
| 2013/0211863 A1 | 8/2013 | White |
| 2013/0265174 A1 | 10/2013 | Scofield et al. |
| 2013/0268325 A1 | 10/2013 | Dembo |
| 2013/0275156 A1 | 10/2013 | Kinkaid et al. |
| 2013/0304522 A1 | 11/2013 | Cundle |
| 2013/0311264 A1 | 11/2013 | Solomon et al. |
| 2014/0038781 A1 | 2/2014 | Foley |
| 2014/0052500 A1 | 2/2014 | Vallapuzha et al. |
| 2014/0075528 A1 | 3/2014 | Matsuoka |
| 2014/0098009 A1 | 4/2014 | Prest et al. |
| 2014/0229258 A1 | 4/2014 | Seriani |
| 2014/0122190 A1 | 5/2014 | Wolfson et al. |
| 2014/0129302 A1 | 5/2014 | Amin et al. |
| 2014/0149157 A1 | 5/2014 | Shaam et al. |
| 2014/0162598 A1 | 6/2014 | Villa-Real |
| 2014/0220516 A1 | 8/2014 | Marshall et al. |
| 2014/0236641 A1 | 8/2014 | Dawkins |
| 2014/0244413 A1 | 8/2014 | Senior |
| 2014/0310019 A1 * | 10/2014 | Blander .................. G06Q 10/10 705/2 |
| 2014/0324633 A1 | 10/2014 | Pollak et al. |
| 2014/0349672 A1 | 11/2014 | Kern et al. |
| 2015/0006428 A1 | 1/2015 | Miller et al. |
| 2015/0016777 A1 | 1/2015 | Abovitz et al. |
| 2015/0058051 A1 | 2/2015 | Movshovich |
| 2015/0097864 A1 | 4/2015 | Alaniz |
| 2015/0161564 A1 | 6/2015 | Sweeney et al. |
| 2015/0178642 A1 | 6/2015 | Abboud |
| 2015/0198459 A1 | 7/2015 | MacNeille et al. |

(56) References Cited

U.S. PATENT DOCUMENTS

| | | |
|---|---|---|
| 2015/0206443 A1 | 7/2015 | Aylesworth et al. |
| 2015/0220916 A1 | 8/2015 | Prakash et al. |
| 2015/0241236 A1 | 8/2015 | Slusar et al. |
| 2015/0248689 A1 | 9/2015 | Paul et al. |
| 2015/0260474 A1 | 9/2015 | Rublowsky et al. |
| 2015/0269865 A1 | 9/2015 | Volach et al. |
| 2015/0324831 A1 | 11/2015 | Barua et al. |
| 2015/0348282 A1 | 12/2015 | Gibbon et al. |
| 2015/0371186 A1 | 12/2015 | Podgurny et al. |
| 2016/0041628 A1 | 2/2016 | Verma |
| 2016/0117657 A1 | 4/2016 | Forbes, Jr. et al. |
| 2016/0117756 A1 | 4/2016 | Carr et al. |
| 2016/0162989 A1 | 6/2016 | Cole et al. |
| 2016/0171891 A1 | 6/2016 | Banatwala et al. |
| 2016/0203422 A1 | 7/2016 | Demarchi et al. |
| 2016/0224935 A1 | 8/2016 | Burnett |
| 2016/0225115 A1 | 8/2016 | Levy et al. |
| 2016/0307276 A1 | 9/2016 | Young |
| 2016/0297316 A1 | 10/2016 | Penilla et al. |
| 2016/0300296 A1 | 10/2016 | Alonso Cembrano |
| 2016/0307288 A1 | 10/2016 | Yehuda et al. |
| 2016/0307373 A1 | 10/2016 | Dean et al. |
| 2016/0321609 A1 | 11/2016 | Dube et al. |
| 2016/0349835 A1 | 12/2016 | Shapira |
| 2016/0364679 A1 | 12/2016 | Cao |
| 2017/0019496 A1 | 1/2017 | Orbach |
| 2017/0039770 A1 | 2/2017 | Lanier et al. |
| 2017/0046658 A1 | 2/2017 | Jones et al. |
| 2017/0046664 A1 | 2/2017 | Haldenby et al. |
| 2017/0046799 A1 | 2/2017 | Chan et al. |
| 2017/0046806 A1 | 2/2017 | Haldenby et al. |
| 2017/0048216 A1 | 2/2017 | Chow et al. |
| 2017/0061509 A1 | 3/2017 | Rosenberg et al. |
| 2017/0089710 A1 | 3/2017 | Slusar |
| 2017/0122746 A1 | 5/2017 | Howard et al. |
| 2017/0146360 A1 | 5/2017 | Averbuch |
| 2017/0232300 A1 | 8/2017 | Tran et al. |
| 2017/0243286 A1 | 8/2017 | Castinado et al. |
| 2017/0243310 A1 | 8/2017 | Dawkins |
| 2017/0249626 A1 | 8/2017 | Marlatt |
| 2017/0276500 A1 | 9/2017 | Margalit et al. |
| 2017/0293881 A1 | 10/2017 | Narkulla |
| 2017/0293950 A1 | 10/2017 | Rathod |
| 2017/0330274 A1 | 11/2017 | Conant, II et al. |
| 2018/0012149 A1 | 1/2018 | Yust |
| 2018/0013211 A1 | 1/2018 | Ricci |
| 2018/0025417 A1 | 1/2018 | Brathwaite et al. |
| 2018/0046431 A1 | 2/2018 | Thagadur Shivappa et al. |
| 2018/0053226 A1 | 2/2018 | Hutton et al. |
| 2018/0053237 A1 | 2/2018 | Hayes et al. |
| 2018/0068355 A1 | 3/2018 | Garry |
| 2018/0075695 A1 | 3/2018 | Simpson |
| 2018/0095471 A1 | 4/2018 | Allan et al. |
| 2018/0102053 A1 | 4/2018 | Hillman et al. |
| 2018/0111494 A1 | 4/2018 | Penilla et al. |
| 2018/0117447 A1 | 5/2018 | Bao et al. |
| 2018/0121958 A1 | 5/2018 | Aist et al. |
| 2018/0129276 A1 | 5/2018 | Nguyen et al. |
| 2018/0140903 A1 | 5/2018 | Poure |
| 2018/0143029 A1 | 5/2018 | Nikulin et al. |
| 2018/0157999 A1 | 6/2018 | Arora |
| 2018/0173742 A1 | 6/2018 | Liu et al. |
| 2018/0173800 A1 | 6/2018 | Chang et al. |
| 2018/0240542 A1 | 8/2018 | Grimmer |
| 2018/0278984 A1 | 9/2018 | Aimone et al. |
| 2018/0293638 A1 | 10/2018 | Simpson |
| 2018/0313798 A1 | 11/2018 | Chokshi et al. |
| 2018/0342106 A1 | 11/2018 | Rosado |
| 2018/0348863 A1 | 12/2018 | Aimone et al. |
| 2018/0357899 A1 | 12/2018 | Krivacic et al. |
| 2018/0365598 A1 | 12/2018 | Jamail |
| 2018/0365904 A1 | 12/2018 | Holmes |
| 2018/0374268 A1 | 12/2018 | Niles |
| 2019/0047427 A1 | 2/2019 | Pogorelik |
| 2019/0050634 A1 | 2/2019 | Nerayoff et al. |
| 2019/0066528 A1 | 2/2019 | Hwang et al. |
| 2019/0102946 A1 | 4/2019 | Spivack et al. |
| 2019/0108686 A1 | 4/2019 | Spivack et al. |
| 2019/0139448 A1 | 5/2019 | Marshall et al. |
| 2019/0143828 A1 | 5/2019 | Sawada et al. |
| 2019/0146974 A1 | 5/2019 | Chung et al. |
| 2019/0158603 A1 | 5/2019 | Nelson et al. |
| 2019/0160958 A1 | 5/2019 | Chaudhary et al. |
| 2019/0178654 A1 | 6/2019 | Hare |
| 2019/0188450 A1 | 6/2019 | Spivack et al. |
| 2019/0205798 A1 | 7/2019 | Rosas-Maxemin et al. |
| 2019/0228269 A1 | 7/2019 | Brent et al. |
| 2019/0236741 A1 | 8/2019 | Bowman et al. |
| 2019/0236742 A1 | 8/2019 | Tomskii et al. |
| 2019/0271553 A1 | 9/2019 | Simpson |
| 2019/0304000 A1 | 10/2019 | Simpson |
| 2019/0311431 A1 | 10/2019 | Simpson |
| 2019/0318286 A1 | 10/2019 | Simpson |
| 2019/0333166 A1 | 10/2019 | Simpson |
| 2019/0333181 A1 | 10/2019 | Simpson |
| 2019/0353499 A1 | 11/2019 | Stenneth |
| 2020/0013498 A1 | 1/2020 | Gelber |
| 2020/0027096 A1 | 1/2020 | Cooner |
| 2020/0047055 A1 | 2/2020 | Ward |
| 2020/0098071 A1 | 3/2020 | Jackson |
| 2020/0125999 A1 | 4/2020 | Simpson |
| 2020/0151816 A1 | 5/2020 | Simpson |
| 2020/0156495 A1 | 5/2020 | Lindup |
| 2020/0160461 A1 | 5/2020 | Kaniki |
| 2020/0173808 A1 | 6/2020 | Beaurepaire et al. |
| 2020/0317074 A1 | 10/2020 | Miller et al. |
| 2020/0317075 A1 | 10/2020 | Yokoyama et al. |
| 2020/0389301 A1 | 12/2020 | Detres et al. |
| 2021/0012278 A1 | 1/2021 | Alon et al. |
| 2021/0041258 A1 | 2/2021 | Simpson |
| 2021/0042835 A1 | 2/2021 | Simpson |
| 2021/0158447 A1 | 5/2021 | Simpson |
| 2021/0166317 A1 | 6/2021 | Simpson |
| 2021/0248633 A1 | 8/2021 | Simpson |
| 2021/0318132 A1 | 10/2021 | Simpson |
| 2021/0379447 A1 | 12/2021 | Lee |
| 2022/0020073 A1 | 1/2022 | Farmer |
| 2022/0100731 A1 | 3/2022 | Tirapu Azpiroz et al. |
| 2022/0122026 A1 | 4/2022 | Okabe et al. |
| 2023/0157579 A1 | 5/2023 | Sato |

FOREIGN PATENT DOCUMENTS

| | | |
|---|---|---|
| JP | 2003177034 A | 12/2001 |
| WO | 2001041084 A2 | 6/2001 |
| WO | 2015059691 A1 | 4/2015 |
| WO | 2015161307 A1 | 4/2015 |
| WO | 2018024844 A1 | 2/2018 |
| WO | 2019/134005 A1 | 7/2019 |
| WO | 2019183468 A1 | 9/2019 |
| WO | 2021/163675 A1 | 8/2021 |

OTHER PUBLICATIONS

Change the World, https://fortune.com/change-the-world/2019/ibm/, Fortune Media IP Limited, pp. 1-5, 2022.

IBM Food Trust, https://www.constellationr.com/node/17601/vote/application/view/588, Constellation Research Inc., pp. 1-4, 2010-2022.

Dey, Somdip, et al., FoodSQRBlock: Digitizing Food Production and the Supply Chain with Blockchain and QR Code in the Cloud, https://www.mdpi.com/2071-1050/13/6/3486/htm, MDPI, pp. 1-27, Mar. 22, 2021.

Wyzant, https://web.archive.org/web/20190327185429/https://www.wyzant.com/hotitworks/students, Wyzant tutoring, pp. 1-13 , Mar. 27, 2019.

PCT International Search Report and Written Opinion; PCT/US2021/065855; dated Mar. 29, 2022.

PCT International Search Report and Written Opinion; PCT/US2022/012717; dated Mar. 30, 2022.

(56) References Cited

OTHER PUBLICATIONS

The Wayback Machine, Interest Rate Swaps, https://web.archive.org/web/20171006212154/https://global.pimco.com/en/gbl/resources/education/understanding-interest-rate-swaps, 2016, pp. 1-7.

Freight Derivatives—a Vital Tool for YOur Business, https://www.reedsmith.com/-/media/files/perspectives/2007/02/freight-derivatives--a-vital-tool-for-your-business/files/freight-derivatives--a vital-tool-for-your-business/fileattachment/etcfreightderivativesavitaltoolforyourbusiness.pdf (Year: 2007), Energy, Trade & Commodities, pp. 1-3.

Barry, Kieth, App lets drivers auction public parking spaces, Wired, Aug. 11, 2011, pp. 1-4.

Jiang, Landu, et al., Sun Chase: Energy-Efficient Route Planning for solar-powered Evs, IEEE 37th international conference on distrubuted computing systems, 2017, pp. 1-11.

PCT International Search Report and Written Opinion; PCT/US2022/027077; dated Nov. 1, 2022.

PCT International Search Report and Written Opinion; PCT/US2022/052969; dated Mar. 21, 2023.

Wei, et al. "impact of aircraft size and seat availability on airlines demand and market share in duopoly markets" Published by Elsevier, 2005, pp. 315-327.

Little, T.D., et al., On the Joys of Missing Data, Journal of pediatric psychology, 2014, pp. 151-162.

Honaker, J., et al., What to do About Missing Values in Time-Series Cross-Section Data, American Journal of Political Science, Sep. 6, 2008, pp. 561-581.

Westerhoff, Market Depth and Price Dynamics: A Note, University of Osnabrueck, Department of Economics Rolandstrasse 8, D-49069 Osnabrueck, German, Mar. 30, 2004, pp. 1-8.

PCT International Search Report and Written Opinion; PCTUS2022/051998; dated Mar. 8, 2023.

EP23153137.7 European Search Report, dated May 24, 2023, pp. 1-10.

EP20787830.7 European Search Report, dated May 12, 2023, pp. 1-10.

Zheyong, Bian, et al., "Planning the Ridesharing Route for the First-Mile Service Linking to Railway Passenger Transportation," Joint Rail Conference, Apr. 2017, pp. 1-11.

EP23168879.7 European Search Report, dated Jul. 5, 2023, pp. 1-13.

Peters, et al.; Student Support Services for Online Learning Re-Imagined and Re-Invigorated: Then, Now and What's to Come; Contact North | Contact Nord; Sep. 2017, 17 pages.

Fleishman; Use Parking Apps to Find Lots, Garages, Valet, and Meters; Macworld; Jul. 19, 2015, 9 pages.

Borras, et al. Intelligent Tourism Reminder Systems: A Survey; Expert Systems with Applications 41; Elsevier, Jun. 9, 2014, 20 pages.

Ramasubramanian, Vasant, "Quadrasense: Immersive UAV-based cross-reality environmental sensor networks," phD diss., Massachusetts Institute of Technology, pp. 1-75, 2015.

Zhao, et al., Incentives in Ridesharing with Deficit Control, Proceedings of the 13th International Conference on Autonomous Agents and Multiagent Systems (AAMAS 2014), May 5-9, 2014, pp. 1021-1028.

Li, Jundong, et al., "Multi-network Embedding", pp. 1-9, 2018.

Papa, U., & Del Core, G., "Design of Sonar Sensor Model for Safe Landing of an UAV," IEEE Metrology for Aerospace, 2015, pp. 346-350.

PCT International Search Report and Written Opinion; PCT/US2020/027543; dated Jul. 1, 2020.

PCT International Search Report and Written Opinion; PCT/US2020/023223; dated Jun. 19, 2020.

PCT International Search Report and Written Opinion; PCT/US2020/023729; dated Jun. 18, 2020.

PCT International Search Report and Written Opinion; PCT/US2020/021546; dated Jun. 8, 2020.

PCT International Search Report and Written Opinion; PCT/US2020/018012; dated Apr. 21, 2020.

PCT International Search Report and Written Opinion; PCT/US2020/012208; dated Mar. 24, 2020.

Westerman; Longitudinal Analysis of Biomarker Data from a Personalized Nutrition Platform in Healthy Subjects; Nature, Scientific Reports; vol. 8; Oct. 2, 2018 (retrieved Jun. 10, 2020). https://www.nature.com/articles/s41598-018-33008-7, 10 pages.

Ahmed, et al.; Energy Trading with Electric Vehicles in Smart Campus Parking Lots; Applied Sciences; Sep. 7, 2018, 17 pages.

Fitzsimmons; Uber Hit with Cap as New York City Takes Lead in Crackdown; New York Times; Aug. 8, 2018 (retrieved Feb. 29, 2020). https://www.wral.com/uber-hit-with-cap-as-new-york-city-takes-lead-in-crackdow/17755819/?version=amp?, 6 pages.

Soccer ball-shaped drone might be the safest flying robot yet https://mashable.com/2015/12/21/soccer-ball-drone/ ; 2015, 2 pages.

Pentland; After Decades of Doubt, Deregulation Delivers Lower Electricity Rates; Forbes; Oct. 13, 2013 (retrieved Feb. 29, 2020). https://www.forbes.com/sites/williampentland/2013/10/13/after-decades-of-doubt-deregulation-delivers-lower-electricity-prices/#201d4a9c1d13, 3 pages.

Sun, et al.; Real-Time MUAV Video Augmentation with Geo-Information for Remote Monitoring; 2013 Fifth International Conference on Geo-Information Technologies for Natural Disaster Management; pp. 114-118; IEEE; 2013.

U.S. Appl. No. 60/035,205, filed Jan. 10, 1997; Page.

Aratani, Lori, "This app wants to reward you for smart commuting choices," The Washington Post, Aug. 18, 2018, pp. 1-3.

Speediance, All-in-One Smart Home Gym; retrieved from internet: https://www.amazon.com/Speediance-Equipment-Resistance-Training-Machine-Works/dp/B0C4KF7844/?th=1; May 8, 2023; p. 1.

Freebeat, Smart Exercise Bike; retrieved from internet: https://www.amazon.com/Resistance-Cushioned-Detection-Altorithm-Instructors/dp/BOBZKKZ6B3/7th=1, Mar. 3, 2023; p. 1.

* cited by examiner

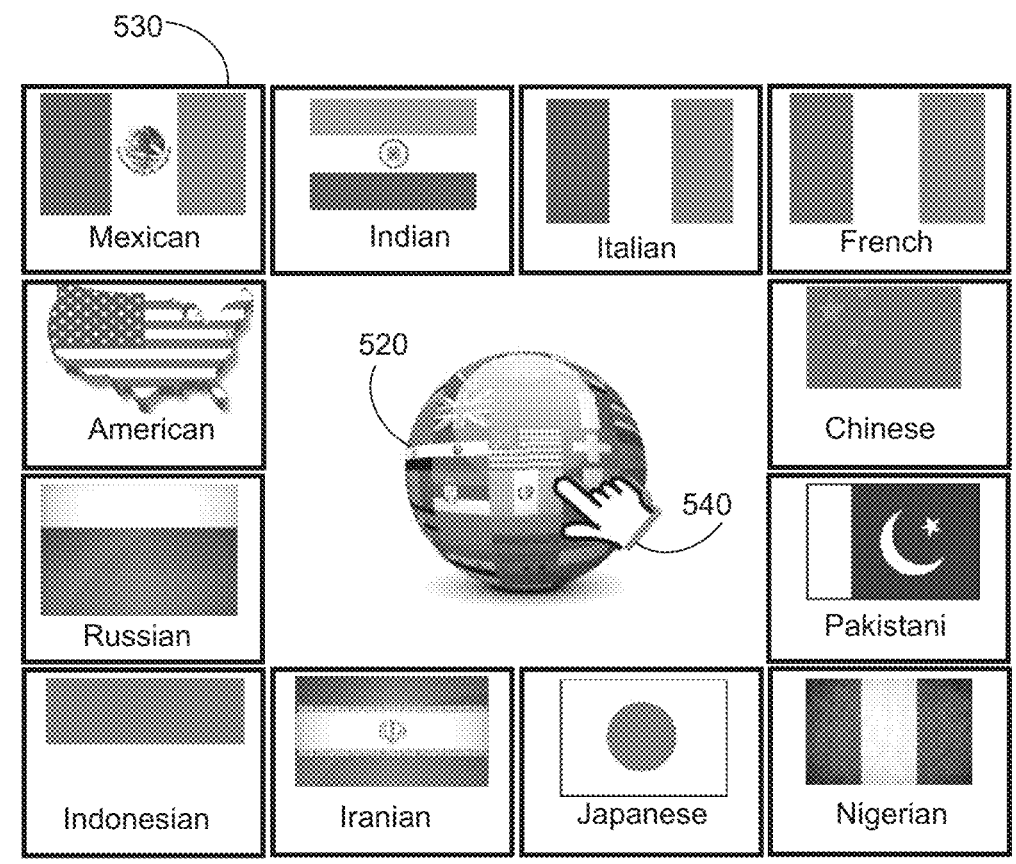
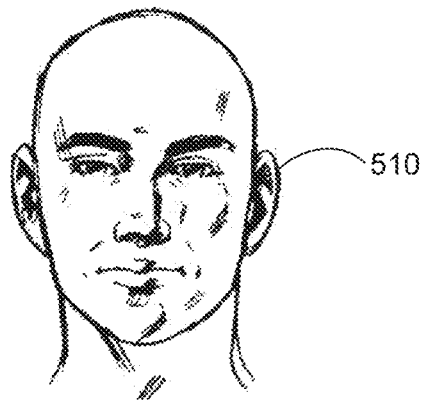
FIG. 5

Maximize Foodie Score, User utility, Nutrition Content, flavoring, ethnicity, variety, style, preference, health, delivery Subject to the following possible constraints

| | | |
|---|---|---|
| Blood Type | Phosphorus | Platelets |
| HDL Cholesterol | Thyroid | Hemoglobin |
| Iron | Vitamin B12 | Hematocrit |
| Ketones | Amylase | Mean Corpuscular Volume |
| LDL Cholesterol | Serum Protein | Blood Glucose |
| Magnesium | Complete Blood Count (CBC) | |
| Potassium | Red Blood Cells | Calcium |
| Progesterone | White Blood Cells | Electrolytes |
| Creatine Kinase | Triglycerides | Allergen Profile |
| Troponin | Coagulation Panel | Celiac, budget |
| HLA-DQ8 gene | HLA-DQ2 gene | Sum of Ingredient weights = 1 |
| Allergies | other | |

$$F_{foodie\ score} = E(B_{Blood\ Chemistry}) - 0.005A\ \sigma^2_{Blood\ chemistry}$$

Take an initial Blood Chemistry with a vector of attributes and assume two possible results after eating meal that is a meal with a vector of blood chemistry attributes.

With a probability p

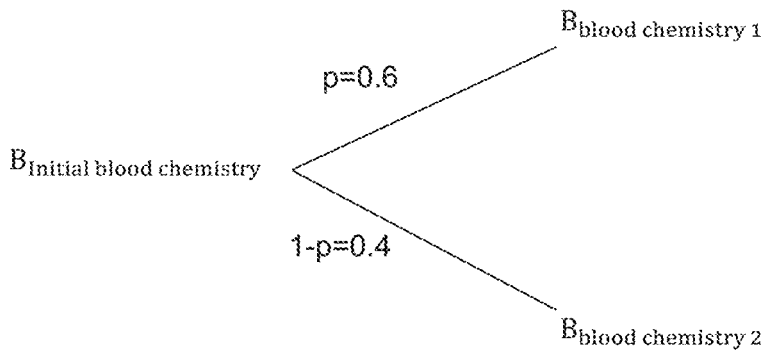

FIG. 14B

1430 So the expected value of Blood Chemistry is:

$$E(B_{Blood\ Chemistry}) = p(B_{blood\ chemistry\ 1}) + (1 - p)(B_{blood\ chemistry2})$$

The variance $\sigma^2$ of the blood chemistry is $$\sigma^2 = p[B_{blood\ chemistry1} - E(B_{blood\ chemistry})]^2 + (1 - p)[B_{blood\ chemistry2} - E(B_{blood\ chemistry})]^2$$

The standard deviation of blood chemistry is $\sigma = \sqrt{\sigma^2}$

FIG. 14D

Accordingly, if $E_{\text{blood chemistry meal 1}} \geq E_{\text{blood chemistry meal 2}}$ and $\sigma_{\text{blood chemistry meal 1}} \leq \sigma_{\text{blood chemistry meal 2}}$ and at least one inequality is strict, inequality has been ruled out

| $E_{\text{blood chemistry meal}}$ | $\sigma_{\text{blood chemistry meal}}$ | $F_{\text{foodie score}} = E(B_{\text{Blood Chemistry}}) - 0.005A\, \sigma^2_{\text{Blood chemistry}}$ |
|---|---|---|
| 10 | 20.0% | 10 − 0.005 × 4 × 400 = 2 |
| 15 | 25.5% | 15 − 0.005 × 4 × 650 = 2 |
| 20 | 30.0% | 20 − 0.005 × 4 × 900 = 2 |
| 25 | 33.9% | 25 − 0.005 × 4 × 1,150 = 2 |

1710

|  | State 1 | State 2 | State 3 |
|---|---|---|---|
| Rapini Probability | 0.5 | 0.3 | 0.2 |
| Rapini Blood Chemistry Toward target | 25% Increase to target | 10% Increase to target | -25% decrease to target |

The mean or expected return of an ingredient is a probability weighted return in all scenarios:

$$E(r) = \sum_s \Pr(s)\, r(s)$$

Applying the aforementioned formula to 1710 above we have $$E(r_{ingredient}) = 0.5 \times 25 + 0.3 \times 10 + 0.2 \times (-25)$$

The variance of Rapini on blood chemistry is $$\sigma^2 = \sum_s \Pr(s)\, [r(s) - E(r)]^2$$

Applying the aforementioned formula to 1710 above we have $$\sigma^2_{rapini} = (0.5(25 - 10.5)^2 + 0.3(10 - 10.5)^2 + 0.2(-25 - 10.5)^2 = 357.25$$

Or $\sigma_{rapini} = \sqrt{357.25} = 18.99\%$

$$E(r_{meal}) = 0.5(E(r_{rapini})) + 0.5(E(r_{chocolate}))$$

$= 0.5 \times 10.5 + 0.5 \times 5 = 7.75\%$, when Rapini is combined with chocolate

$$\sigma_{Foodie} = 0.5(\sigma_{rapini}) + 0.5(\sigma_{chocolate})$$

The standard deviation of the combination of ingredients

$$[r_{rapini} - E(r_{rapini})][r_{chocolate} - E(r_{chocolate})]$$

$$Cov(r_{rapini}, r_{chocolate}) = \sum_{s} \Pr(s) \, [r_{rapini}(S) - E(r_{rapini})][r_{chocolate}(s) - E(r_{chocolate})]$$

FIG. 18D $$\rho(\text{rapini}, \text{chocolate}) = \frac{\text{Cov}[r_{\text{rapini}}, r_{\text{chocolate}}]}{\sigma_{\text{rapini}} \sigma_{\text{chocolate}}}$$

1910

FIG. 19A $$\sigma^2_{\text{blood chemistry}} = w_1^2 \sigma^2 + w_2^2 \sigma_2^2 + 2 w_1 w_2 \text{Cov}(r_1 r_2)$$

Where subscript 1 is rapini or another ingredient and

Subscript 2 is chocolate or another ingredient

1920

FIG. 19B $$\max_{\text{vector of ingredients}} [F_{\text{foodie Score}}] = E\left( r_{\substack{\text{Blood} \\ \text{chem} \\ \text{meal}}} \right) - 0.005 A \sigma^2_{\substack{\text{blood} \\ \text{chem} \\ \text{meal}}}$$

Where term A is the Foodie's user preference index

|  | meal$_1$ or ing$_1$ | meal$_2$ or ing$_2$ |
|---|---|---|
| Meal or ingredient weights | w$_{ing\,1}$ | w$_{ing2}$ |
| w$_{ing\,1}$ | $\sigma^2_{ing\,1}$ | $Cov(r_{ing\,1}, r_{ing\,2})$ |
| w$_{ing\,2}$ | $Cov(r_{ing\,1}, r_{ing\,2})$ | $\sigma^2_{ing\,2}$ |

|  | Ingredient 1 | Ingredient 2 |
|---|---|---|
| Expected blood chemistry; E(r) | 8% | 13% |
| Standard deviation ; $\sigma$ | 12% | 20% |
| Covariance; $Cov(r_{ing1}, r_{ing2})$ | 72 | |
| Correlation Coefficient ; $\rho_{ing1,ing2}$ | 0.30 | |

| $w_{rapini}$ | $w_{chocolate}$ | $\rho = -1$ | $\rho = 0$ | $\rho = 0.3$ | $\rho = 1$ |
|---|---|---|---|---|---|
| 0.0 | 1.00 | 20.00% | 20.00% | 20.00% | 20.00% |
| 0.25 | 0.75 | 12.00 | 15.3 | 16.16 | 18.00 |
| 0.50 | 0.50 | 4 | 11.66 | 13.11 | 16.00 |
| 0.75 | 0.25 | 4.00 | 10.30 | 11.53 | 14.00 |
| 1.00 | 0.0 | 12.00 | 12.00 | 12.00 | 12.00 |
| Minimum $\sigma_m$ | | 0.00 | 10.29 | 11.45 | - |
| $w_{rapini}$@min$\sigma_m$ | | 0.63 | 0.74 | 0.82 | - |

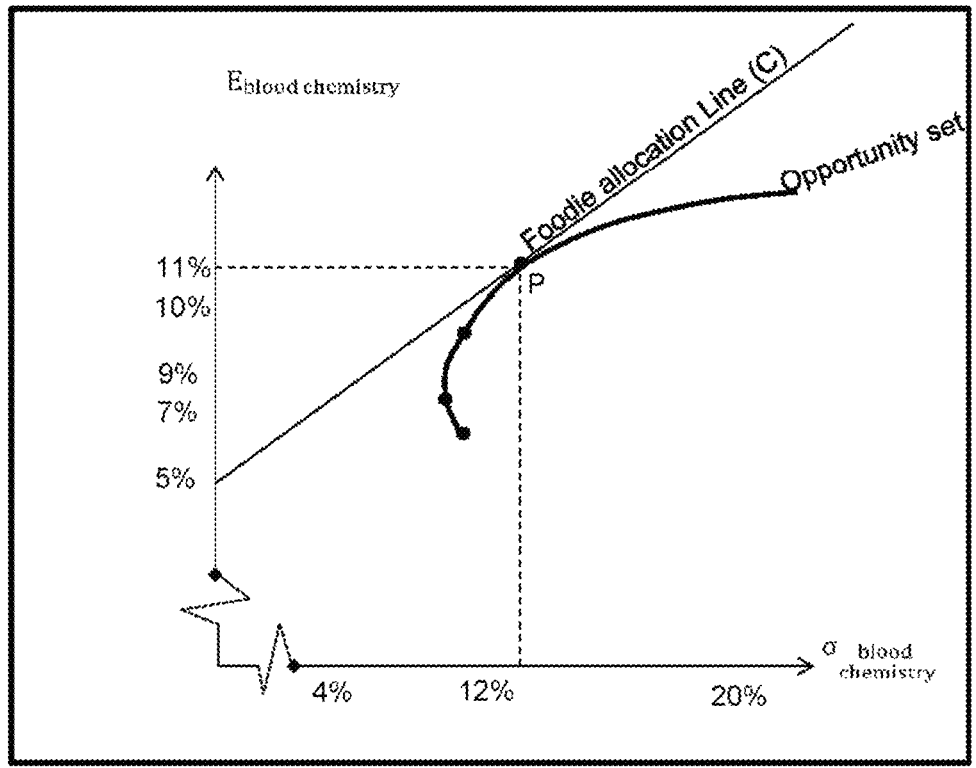

FIG. 24A $$\text{Slope}_{\text{Foodie allocation line}} = \frac{E_{\text{blood chemistry}} - \text{Water}_{\text{blood chemistry}}}{\sigma_{\text{blood chemistry}}}$$

$$E_{\text{blood chemistry(BC)}} \text{ of combination} = w_{\text{rapini}} E_{\text{rapini(BC)}} + w_{\text{chocolate}} E_{\text{chocolate(BC)}}$$

$$= 8 w_{\text{rapini}} + 13 w_{\text{chocolate}}$$

$$\sigma_{\text{blood chemistry combination}} = [w_{\text{rap}}^2 \sigma_{\text{rap}}^2 + w_{\text{choc}}^2 \sigma_{\text{choc}}^2 + 2 w_{\text{rap}} w_{\text{choc}} \text{Cov}(r_{\text{rap}} r_{\text{choc}})]^{\frac{1}{2}}$$

$$= [144 w_{\text{rap}}^2 + 400 w_{\text{choc}}^2 + 2 \times 72 w_{\text{rap}} w_{\text{choc}}]^{\frac{1}{2}}$$

FIG. 24B $$\max_{w_i} \text{Slope}_{\text{Foodie allocation line}} = \frac{E_{\text{blood chemistry}} - \text{Water}_{\text{blood chemistry}}}{\sigma_{\text{blood chemistry}}}$$

Subject to $\sum w_i = 1$, which is the standard problem in calculus.

2510

FIG. 25A $$w_{\text{rapini}} = \frac{[E(r_{\text{rapBC}}) - \text{Water}_{\text{BC}}]\sigma^2_{\text{chocBC}} - [E(r_{\text{chocBC}}) - \text{Water}_{\text{BC}}]\text{Cov}(r_{\text{rapBC}}, r_{\text{chocBC}})}{[E(r_{\text{rapBC}}) - \text{Water}_{\text{BC}}]\sigma^2_{\text{chocBC}} + [E(r_{\text{chocBC}}) - \text{Water}_{\text{BC}}]\sigma^2_{\text{rapBC}} - [E(r_{\text{rapBC}}) - \text{Water}_{\text{BC}} + E(r_{\text{chocBC}}) - \text{Water}_{\text{BC}}]\text{Cov}(r_{\text{rapBC},\text{chocBC}})}$$

$$w_{\text{chocolate}} = 1 - w_{\text{rapini}}$$

$$w_{\text{rapini}} = \frac{(8-5)400 - (13-5)72}{(8-5)400 + (13-5)144 - (8-5+13-5)72}$$
$$= 0.40$$
$$w_{\text{chocolate}} = 1 - 0.40 = 0.6$$

2520

FIG. 25B $$y = \frac{E(r_{\text{combination meal}}) - \text{Water}_{\text{BC}}}{0.01 \times A\sigma^2_{\text{combination meal}}}$$

$$= \frac{11-5}{0.01 \times 4 \times 14.2^2} = 0.7439$$

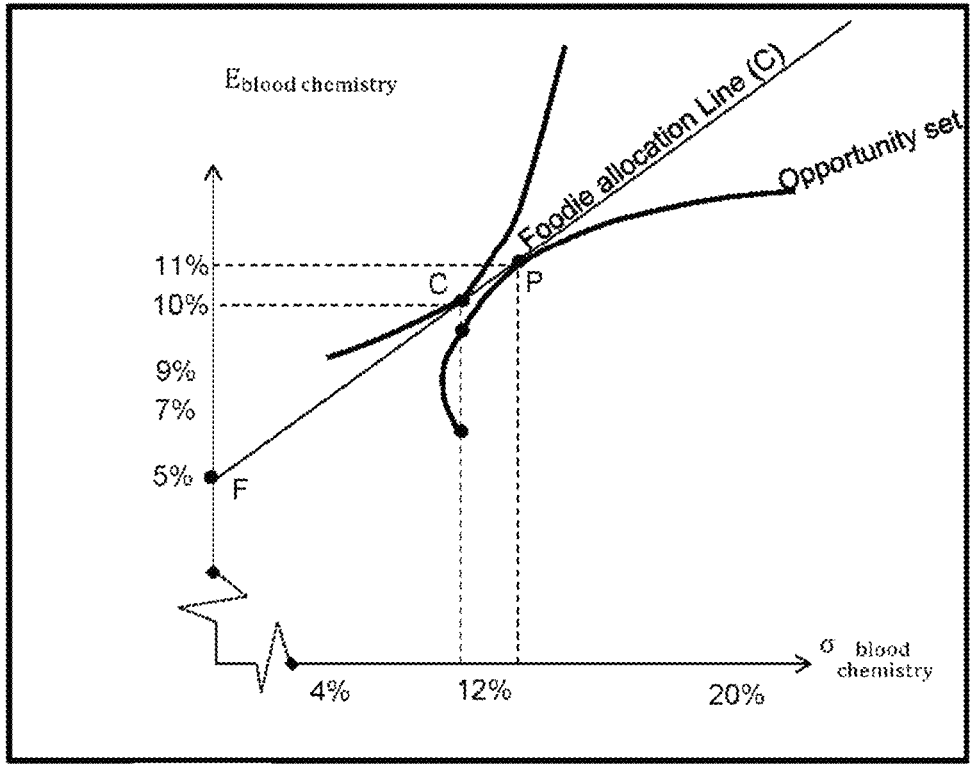

FIG. 26A

Specify the blood chemistry of all ingredients (expected blood chemistry, variances and covariances)

Establish the combination of ingredients

Calculate the optimal ingredient combination

Calculate the properties of the ingredient combination using weights determined by optimization.

Allocate calories between ingredient combo and water.

Calculate the fraction of the complete meal towards the ingredients and water

Calculate the share of calories in each ingredient and water

FIG. 26B $$E(r_p) = \sum_{i=1}^{n} w_i E(r_i)$$

$$\sigma_p^2 = \sum_{i=1}^{n} w_i^2 \sigma_i^2 + \sum_{\substack{i=1 \\ i \neq j}}^{n} \sum_{j=1}^{n} w_i w_j \mathrm{Cov}(r_i, r_j)$$

2810

2820

$$w \in R^d$$

Vector w is a set of ingredient weights $w = \begin{bmatrix} w_1 \\ w_2 \\ \vdots \\ w_d \end{bmatrix}$ where $w_1 + w_2 + \cdots + w_d = 1$ Let the expected meal ingredient blood and saliva chemistry vector be $$r = \begin{bmatrix} r_1 \\ r_2 \\ \vdots \\ r_d \end{bmatrix}, E(r) = \begin{bmatrix} E(r_1) \\ E(r_2) \\ \vdots \\ E(r_d) \end{bmatrix}$$

Variance – covariance Matrix of ingredients in the meal ingredient combination $$\sum = \begin{bmatrix} \sigma_1^2 & \cdots & \sigma_1 \\ \vdots & \ddots & \vdots \\ \sigma_1 & \cdots & \sigma_d^2 \end{bmatrix}$$

$$r_p = w'x\,r = [w_1 \quad \cdots \quad w_d] x \begin{bmatrix} r_1 \\ \vdots \\ r_d \end{bmatrix}$$

$$E(r_p) = w'x\,E(r)$$

$$\sigma_p^2 = w'x \sum x\,w = [w_1 \ldots w_d] \begin{bmatrix} \sigma_1^2 & \cdots & \sigma_1 \\ \vdots & \ddots & \vdots \\ \sigma_1 & \cdots & \sigma_d^2 \end{bmatrix} \begin{bmatrix} w_1 \\ \vdots \\ w_d \end{bmatrix}$$

SYSTEM AND METHOD FOR BLOOD AND SALIVA OPTIMIZED FOOD CONSUMPTION AND DELIVERY

BACKGROUND OF THE INVENTION

Field of the Invention

Implementations of various methods to utilize blood sampling and saliva sampling analysis to optimize personal food nutrition, health, variety, ethnicity, flavors and delivery using iterative artificial intelligence and data mining. Western civilization wastes nearly 40% of produced and harvested food. The Center for Disease Control and Prevention cites that 36.5% of adults in the West suffer from obesity. The estimated annual medical cost of obesity in the U.S. was $147 billion in 2008 U.S. dollars. The medical costs of the aforementioned obese individuals are $1,429 higher than for those of normal weight. While Western developed markets show quantitative data that points to excess, developing nations still suffer from stunted growth, lack of nutrition, agricultural shortfalls and lack of stability in food supply. There are tremendous opportunities to re-allocate nutrition using math, science and technology to meet the world's needs without necessarily producing more, but improving efficiency and utilization rates. The implementation of the method allows for unbiased measure of nutrition and body chemistry through blood work and saliva sampling analysis and computerized systems where artificial intelligence based optimization techniques for improvement of human condition and health are utilized. No two people are alike in our unique body chemistry and yet we ingest food to serve our unique chemistries without unbiased analysis that is at our fingertips with the proposed method and system. The implementation of the method uses biomarkers and chemistry in blood work and saliva to determine optimal personal food consumption, ingredient weighting, health, variety, flavoring, style, ethnicity, nutrition and delivery which does not rely on self-reporting problems of inaccurate recall or reluctance to give a candid report. The biomarker analysis provides for an unbiased yet statistically accurate history which is stable and more reliable than self-reporting. Implementations of the various methods to create optimal food nutrition, health, ingredient weighting, variety, ethnicity, flavor and delivery also may reduce food consumption by 5% to 70% depending on the variables. The method also provides unbiased ordering information that is based on science from the user to reduce food waste in grocery stores by as much as 5% to 40%, but not limited to those levels of reduction. Reduced food waste lowers food cost globally, reduces fossil fuel consumption and provides more resources for those who have very little resources or not enough resources. Implementations or various methods of optimizing personal food intake for blood chemistry and saliva analysis also provide optimal healthy food intake which improves the overall quality of a society. Implementations of methods to optimize food intake for blood chemistry and saliva analysis also reduce mood swings caused by excessive variation in blood chemistry. Lower amounts of mood swings due to lower variation in blood chemistry contribute positively to higher human productivity and lower amounts of societal stress. For the purpose of efficiency in this document we will interchangeably use the term "User" and "Foodie".

Description of the Related Art

The following descriptions and examples are not admitted to be prior art by virtue of their inclusion within this section.

The current implementations of methods to use biomarkers, blood testing and saliva testing focus on treating specific conditions and diagnosing predispositions, but they are not used to optimize human health using algorithms and artificial intelligence neural networks to provide iterative system feedback from a user to then compare utility maximization equations over blood and saliva variables subject to a plurality of constraints, such as budget, nutrient matching to blood type and chemistry, over a computer system where users may have a simple way to order raw or cooked food over the application and arrange for delivery, yet harness the power of the calculus maximization equations and neural networks to optimize their blood chemistry and health in the background. Further, the system recommends various food options based on non-linear systems of vectors, neural networks and optimization formulas to optimize on all of user preference, health, ingredient weights, variety, flavoring, style, ethnicity, nutrition and delivery.

Implementations of methods have been made in systems that provide the identification of a biomarker for the analysis of certain conditions, but the implementations do not provide a solution for the user to have an integrated approach to their overall health and diet with feedback from artificial intelligence neural network algorithms or calculus maximization equations designed to optimize food intake based on analysis of the user's blood and saliva:

1) U.S. Pat. No. 7,680,690 issued Mar. 16, 2010 to Anthony B. Catalano covers a methodology for customers seeking to purchase a meal from a food service vendor such as a restaurant, a cafeteria, or a vending machine, by ordering a food preparation based upon menu-selection. In addition to receiving ordered food, customers receive suggestions for optionally modifying their food orders based upon nutritional benefits and other criteria. Either during real-time customer-ordering or during post-ordering, a food-service vendor presents a customer's suggestions specific to a pending tentative or completed order, wherein the customer may enjoy purported nutritional benefits by electing to follow these suggestions and thereby modify the tentative order into a corresponding completed order. The preferred embodiment contemplates a restaurant environment in which customers typically approach a food-ordering counter and interface with both a menu display and with order-taking personnel. Other embodiments implicate kiosks, vending machines, remote access devices, and locally and remotely-accessed networked computers, wherein customers interact with automated computer-driven devices instead of, or in addition to, wait-staff or other food service personnel. The limitation and disadvantages of the prior art which seeks to have the user continually modify food choices is that the solution has no direct tie to the user's personal blood or saliva chemistry in the calculation, the prior art does not address a full composite of food attributes, and the prior art system and method does not consider that individual blood and saliva chemistry reacts differently to the plurality of menu ingredients, which renders the solution very limited in scope and use. By contrast, the prior art method of a computerized database of anonymous customer preference information is fundamentally different from the proposed method of a custom blood and saliva database that may provide specific calculations for each user. Also by contrast, the proposed method considers each food selection, considering a specific mathematic optimization equation of the relationship to blood and saliva chemistry of the specific user. Also by contrast, the proposed method has optimized the selection alternatives in advance of the order specifically for blood and saliva chemistry, whereas the aforementioned prior art method modifies a user's selection to pick healthier ingredients but does not consider that each user has fundamentally different blood and saliva chemistry. The process is fundamentally different. Additionally by contrast, the proposed method does not substitute food ordering based on healthier ingredients like the prior art, but recommends foods based on their specific relationship to the user's blood and saliva chemistry. Accordingly the premise and method of the prior art are completely unique and fundamentally different from the proposed method and system.

2) U.S. Pat. Nos. 6,618,062 and 6,646,659 issued Sep. 9, 2003 to Brown, et al. discloses a method, system and program for specifying an electronic food menu with food preferences from a universally accessible database. The prior art relates to a method, system and program for specifying an electronic menu for a particular customer from food preferences received via a person integrated circuit. The technology taught in Brown covers a method, system and program retrieves unique customer preferences based upon a unique customer key which then improves the efficiency of special requests on a menu in the food industry. The proposed method and system is solely based on preferences which are input by the user and these preferences may or may not relate to blood or saliva chemistry. The proposed method and system uses an objective measurement of data from a sample of blood and saliva chemistry which is then utilized in a mathematic optimization equation to move the user's blood chemistry from its current state to a desired target range. Accordingly the premise and method of the prior art are completely unique and fundamentally different from the proposed method and system.

3) U.S. Pat. No. 6,434,530 issued Aug. 13, 2002 to Sloane et al. discloses an interactive system adapted for use in a shopping venue to provide supplemental information related to an article available for selection by shoppers in a shopping venue. The prior art provides a method and system of retrieving helpful data for a consumer to guide their decision process. The prior art describes a method that shows a user that a can of tomato sauce is on sale, then it helps to determine a sort for the best price, lower amount of salt, a name brand, a store brand while referencing the users prior preferences from a database. While the system is interactive and intelligent, the underlying algorithms, purpose and content are different from the proposed method. The proposed method and system directly utilizes a proprietary and confidential blood and saliva sample from the user to then optimize hundreds of combinations and permutations of groupings of ingredients and recipes a user may enjoy that are selected upon reference for the user's consumption, health, variety, flavoring, style, nutrition and delivery, and which does not rely on a single diagnostic test or self-reporting problems because of independent blood and saliva tests subject to the constraints of income, price, and location.

4) U.S. Pat. No. 7,090,638 issued Aug. 15, 2006 to Edward Vidgen covers a dietary planning system that receives the personal characteristics and food preferences for a user. The prior art reviews personal characteristics such as a desired physiological rate of change for the individual and develops optimal dietary menus that maximize the palatability of the menu while satisfying dietary constraints that may relate to a user's preferences. The prior art requests the user to input a desired physiological rate of change such as one pound per week, and the user also inputs his or her energy expenditure by answering questions about the user's activity levels. The equation of the prior art uses a simple formula to target, such as, for example, one pound of weight loss per week as a requirement to produce a diet that reduces kilocalories by 500 units a day. The prior art labels equations that weight various ingredients that are subject to a kilocalorie inequality or a protein weight inequality. However the teaching does not make clear any actual optimization equation, so it is unclear that the system is optimizing anything other than giving weights that fall under a constraint, which does not qualify as optimization. Further, it does not handle potential non-linear relationships of food chemistry and blood chemistry. The prior art system does not discuss or handle any relationship of the user's blood or saliva chemistry with respect to various food ingredients.

5) U.S. Pat. No. 9,410,963 issued Aug. 9, 2016 to Nestec S.A. covers the use of a biomarker to diagnose the likelihood to resist diet induced weight gain and the susceptibility of diet induced weight gain. The method is to determine the level of hexanoylglycine relative to a predetermined reference to determine the likelihood of resisting high fat diet induced weight gain. The proposed method is diagnostic, not prescriptive. The method attempts to diagnose predisposition of likelihood to reduce diet induced weight gain and likelihood to resist high fat diet induced weight gain. By contrast the proposed independent methods and systems form optimization algorithms (which are linear and non-linear systems of vectors) on individual food ingredients and the combinations thereof to maximize nutrition of a user's consumption, health, variety, flavoring, style, nutrition and delivery, which do not rely on a single diagnostic test or self-reporting problems because of independent blood and saliva tests subject to the constraints of income, price, and location. Further, the proposed method and system is fully integrated to allow a user to have their meal selection with as few as three clicks on a graphical user interface while the computer based optimization calculations of linear and non-linear vectors alongside optimization maximization equations have solved for optimal healthy choices.

6) U.S. Pat. No. 6,663,564 issued Dec. 16, 2003 to Weight Watchers Limited covers a process for controlling body weight in which a selection of food servings is based on a calculated point value and a range of allotted daily points which is adjusted for weight change. The calculated point value is a function of measured calories, total fat and dietary fiber. A range of points allotted per day may be calculated based on current body weight, caloric reduction to be achieved, physical activity level and physical activity duration. While the process and method uses a math formula to count kilocalories, fiber, and fat, the equation is linear and therefore does not maximize for overall nutrition considering a more realistic but larger set of variables and the non-linear nature of the real life nutrition equation. Further the method is not customized by blood and saliva chemistry per each user. By contrast the proposed independent methods and systems form optimization algorithms (which are linear and non-linear systems of vectors) on individual food ingredients and the combinations thereof to maximize nutrition of a user's consumption, health, variety, flavoring, style, nutrition and delivery, which do not rely on a single diagnostic test or self-reporting problems because of independent blood and saliva tests subject to the constraints of income, price, and location. Further, the proposed method and system is fully integrated to allow a user to have their meal selection with as few as three clicks on a graphical user interface while the computer based optimization calculations of linear and non-linear vectors alongside optimization maximization equations have solved for optimal healthy choices in the background of the simple graphical user interface.

7) U.S. Pat. No. 5,412,560 issued May 2, 1995 to Dine Systems, Inc. covers a process for evaluating an individual's food choices based upon selected factors and dietary guidelines. The invention analyzes the food an individual eats and determines certain predictor and follower nutrients that will give rise to an assessment of how a person's diet matches with various dietary guidelines established by governmental and/or other entities. The invention provides the results of the analysis to the individual complete with messages regarding over or under consumption of key nutrients so that the individual can correct the diet thereby resulting in better eating habits. The invention also gives the individual a "score" by which the person can immediately assess how well he or she is doing with respect to the various guidelines. The higher the number the better the diet. Further the method is not customized by blood and saliva chemistry per each user. By contrast the proposed independent methods and systems form optimization algorithms (which are linear and non-linear systems of vectors) on individual food ingredients and the combinations thereof to maximize nutrition of a user's consumption, health, variety, flavoring, style, nutrition and delivery, which do not rely on a single diagnostic test or self-reporting problems because of independent blood and saliva tests subject to the constraints of income, price, and location. Further, the proposed system and method is able to log each meal ingredient because the system has the ability to order the food raw or prepared and deliver the food to the user. The proposed system provides an integrated approach to holistic nutrition, and also provides food item intelligence to take a picture of a meal and then log into the database food that was not ordered or designed on the system. Further, the proposed method and system is fully integrated to allow a user to have their meal selection with as few as three clicks on a graphical user interface while the computer based optimization calculations of linear and non-linear vectors alongside optimization maximization equations have solved for optimal healthy choices in the background of the simple graphical user interface.

8) U.S. Pat. No. 9,528,972 issued Dec. 27, 2016 to Eugenio Minvielle covers nutritional substance systems and methods are disclosed enabling the tracking and communication of changes in nutritional, organoleptic, and aesthetic values of nutritional substances, and further enabling the adaptive storage and adaptive conditioning of nutritional substances. The system logs changes in nutrition as heat and cooling changes the nutritional values. Further the method is not customized by blood and saliva chemistry per each user. By contrast the proposed independent methods and systems form optimization algorithms (which are linear and non-linear systems of vectors) on individual food ingredients and the combinations thereof to maximize nutrition of a user's consumption, health, variety, flavoring, style, nutrition and delivery, which do not rely on a single diagnostic test or self-reporting problems because of independent blood and saliva tests subject to the constraints of income, price, and location. Further, the proposed system and method is able to log each meal ingredient because the system has the ability to order the food raw or prepared and deliver the food to the user. The proposed system provides an integrated approach to holistic nutrition and also provides food item intelligence to take a picture of a meal and then log into the database food that was not ordered or designed on the system. Further, the system recommends various food options based on linear and non-linear systems of vectors and optimization formulas to optimize on all of user preference, health, variety, flavoring, style, ethnicity, nutrition and delivery. Further, the proposed method and system is fully integrated to allow a user to have their meal selection with as few as three clicks on a graphical user interface while the computer based optimization calculations of non-linear vectors alongside optimization maximization equations have solved for optimal healthy choices in the background of the simple graphical user interface.

9) U.S. Pat. No. 8,249,946 issued Aug. 21, 2012 to General Mills, Inc. covers a system and method for selecting, ordering and distributing customized food products is disclosed. In one embodiment, the method is a computer-implemented method comprising viewing a list of additives for creating a customized food product, selecting one or more additives from the list of additives to create the customized food product, and transmitting a request to purchase the customized food product, which is then distributed to the consumer. By communicating with the manufacturer as to personal needs and desires pertaining to health, activity level, organoleptic preferences and so forth, the consumer can now develop and order a customized food product to suit his or her particular tastes, using a real-time interactive communication link. Further the method is not customized by blood and saliva chemistry per each user. By contrast the proposed independent methods and systems form optimization algorithms (which are linear and non-linear systems of vectors) on individual food ingredients and the combinations thereof to maximize nutrition of a user's consumption, health, variety, flavoring, style, nutrition and delivery, which do not rely on a single diagnostic test or self-reporting problems because of independent blood and saliva tests subject to the constraints of income, price, and location. Further, the proposed system and method is able to log each meal ingredient because the system has the ability to order the food raw or prepared and deliver the food to the user. The proposed system provides an integrated approach to holistic nutrition and also provides food item intelligence to take a picture of a meal and then log into the database food that was not ordered or designed on the system. Further, the system recommends various food options based on linear and non-linear systems of vectors and optimization formulas to optimize on all of user preference, health, variety, flavoring, style, ethnicity, nutrition and delivery. Further, the proposed method and system is fully integrated to allow a user to have their meal selection with as few as three clicks on a graphical user interface while the computer based optimization calculations of non-linear vectors alongside optimization maximization equations have solved for optimal healthy choices in the background of the simple graphical user interface.

10) U.S. Pat. No. 8,920,175 issued Dec. 30, 2014 to Thrive 365 International, Inc. covers a method is provided for assigning a relative score number to foods. Assignment of a relative score number to foods allows consumers to select foods that will provide a desirable diet. Equations are provided which are effective to yield a predicted raw score based on measured characteristics. The predicted raw score statistically correlates to a raw score that would be determined by an actual panel. The predicted raw scores are further processed to provide a relative score number that can be easily tracked by a consumer. Further the method is not customized by blood and saliva chemistry per each user. By contrast the proposed independent methods and systems form optimization algorithms (which are linear and non-linear systems of vectors) on individual food ingredients and the combinations thereof to maximize nutrition of a user's consumption, health, variety, flavoring, style, nutrition and delivery, which do not rely on a single diagnostic test or self-reporting problems because of independent blood and saliva tests subject to the constraints of income, price, and location. Further, the proposed system and method is able to log each meal ingredient because the system has the ability to order the food raw or prepared and deliver the food to the user. The proposed system provides an integrated approach to holistic nutrition and also provides food item intelligence to take a picture of a meal and then log into the database food that was not ordered or designed on the system. Further, the system recommends various food options based on linear and non-linear systems of vectors and optimization formulas to optimize on all of user preference, health, variety, flavoring, style, ethnicity, nutrition and delivery. Further, the proposed method and system is fully integrated to allow a user to have their meal selection with as few as three clicks on a graphical user interface while the computer based optimization calculations of non-linear vectors alongside optimization maximization equations have solved for optimal healthy choices in the background of the simple graphical user interface.

SUMMARY

The claimed subject matter is not limited to implementations that solve any or all of the noted disadvantages. Further, the summary section is provided to introduce a selection of concepts in a simplified form that are further described below in the detailed description section. The summary section is not intended to identify key features or essential features of the claimed subject matter, nor is it intended to be used to limit the scope of the claimed subject matter.

An independent method and system forming optimization algorithms (which are linear and non-linear systems of vectors) on individual food ingredients and the combinations thereof in recipe format for an order of food from a raw food distribution point or a prepared food distribution point to maximize nutrition of a user's consumption, health, variety, flavoring, style, ethnicity, nutrition and delivery, which do not rely on a single diagnostic test or self-reporting problems because of independent blood and saliva tests subject to further constraints of income, price, and location. Further, the proposed system and method is able to log each meal ingredient because the system has the ability to order the food raw or prepared and deliver the food to the user or allow the user to pick up the food at a food distribution point. The proposed system provides an integrated approach to holistic nutrition and also provides food item intelligence to take a picture of a meal and then log into the database food that was not ordered or designed on the system. Further, the system recommends various food options based on non-linear systems of vectors and optimization formulas to optimize on all of user preference, blood and saliva chemistry, health, variety, flavoring, style, ethnicity, nutrition and delivery among other variables but not limited to the aforementioned variables. Further, the proposed method and system is fully integrated to allow a user to have their meal selection with as few as three clicks on a graphical user interface while the computer based optimization calculations of linear and non-linear vectors alongside optimization maximization equations have solved for optimal healthy choices for the user. For the purpose of efficiency in this document we will interchangeably use the term "User" and "Foodie".

In one implementation, the method and system for determining the optimal nutrition food intake solution may include receiving one or more parameters that describe the user's blood chemistry and saliva chemistry. The blood chemistry and saliva chemistry test data may then be submitted into a database that may be utilized to run a system of linear and non-linear systems of vectors alongside a system of vectors that considers food ingredients, flavor, ethnicity and style preferences in the context of a recipe that optimizes nutrition for a user's blood supply and body chemistry. The output of the applied math equation is a portfolio of blood and saliva optimized recipes or prepared dishes that are either raw or prepared which can then be delivered or picked up at the user's home, a raw food distribution point such as a grocery store or market, or a prepared food establishment such as a restaurant or prepared food kitchen distribution point. The user's budget is part of the optimization equation so that the food choices are optimized over a given budget or level of service.

BRIEF DESCRIPTION OF THE DRAWINGS

Implementations of various technologies will hereafter be described with reference to the accompanying drawings. It should be understood, however, that the accompanying drawings illustrate only the various implementations described herein and are not meant to limit the scope of various technologies described herein. For the purpose of efficiency in this document we will interchangeably use the term "User" and "Foodie".

FIG. 5 illustrates the implementation of methods of a typical user selecting the style and ethnicity of the food choice prior to optimization of the nutrition content utilizing the graphical user interface of the associated application designed for both 2$d$ and 3$d$ smart devices as well as augmented reality and mixed reality interface configurations in accordance with some embodiments.

FIG. 10 illustrates the implementation of methods which may include a plurality of variables and constraint variables in the determining the optimal ingredients to improve the blood and saliva chemistry of a user through linear and non-linear vector maximization and minimization equations in accordance with some embodiments.

FIGS. 14A and 14B and 14C and 14D illustrate an exemplary implementation of methods utilizing a plurality of linear and non-linear equations to maximize nutrition of a user's consumption, health, variety, flavoring, style, ethnicity, nutrition and delivery of prepared and raw food which does not rely on a single diagnostic test or self-reporting problems because of independent blood and saliva tests subject to the constraints of income, price, and location in accordance with some embodiments.

FIGS. 17A and 17B and 17C illustrate one exemplary probability distribution of a particular ingredient affecting the blood chemistry of a Foodie or user as well as the mean of the expected return of ingredients to blood chemistry and the variance of an ingredient to the blood chemistry.

FIGS. 18A and 18B and 18C and 18D illustrate the blood chemistry of a vector of ingredients is the weighted average of the blood chemistry of each individual ingredient and the standard deviation as well as the covariance of ingredients on blood chemistry.

FIGS. 19A and 19B and 19C illustrate how the covariance and correlation equations of food ingredients affect the blood chemistry of the Foodie or user.

FIGS. 20A and 20B illustrate some descriptive statistics of a partial implementation of a simple two ingredient embodiment of the system and method.

FIG. 22B illustrates the ingredient combination opportunity set for various correlation factors.

FIGS. 24A and 24B illustrate the highest sloping Foodie allocation line (C) at point P intersecting with the opportunity set.

FIGS. 25A and 25B and 25C illustrate the framework to maximize the slope of the foodie allocation line subject to the condition that the sum of the weight of all the ingredients will sum to one which is a standard calculus problem.

FIGS. 26A and 26B illustrate the graphical solution of FIGS. 25A and 25B and 25C as well as the summarization of a two or more ingredient embodiment to a general embodiment.

FIG. 29 illustrates the expected general exemplary case of the method with vectors to illustrate any general combination of food chemistry components, ingredients and combinations and how they interact with any blood chemistry components or elements.

FIG. 30 illustrates a specific embodiment of the components of food chemistry elements and their expected values.

FIG. 31 illustrates additional data from the same specific embodiment shown in FIG. 30.

FIG. 32 illustrates additional data from the same specific embodiment shown in FIG. 30 and FIG. 31.

DETAILED DESCRIPTION

The discussion below is directed to certain specific implementations. It is to be understood that the discussion below is only for the purpose of enabling a person with ordinary skill in the art to make and use any subject matter defined now or later by the patent "claims" found in any issued patent herein.

Figure 1:
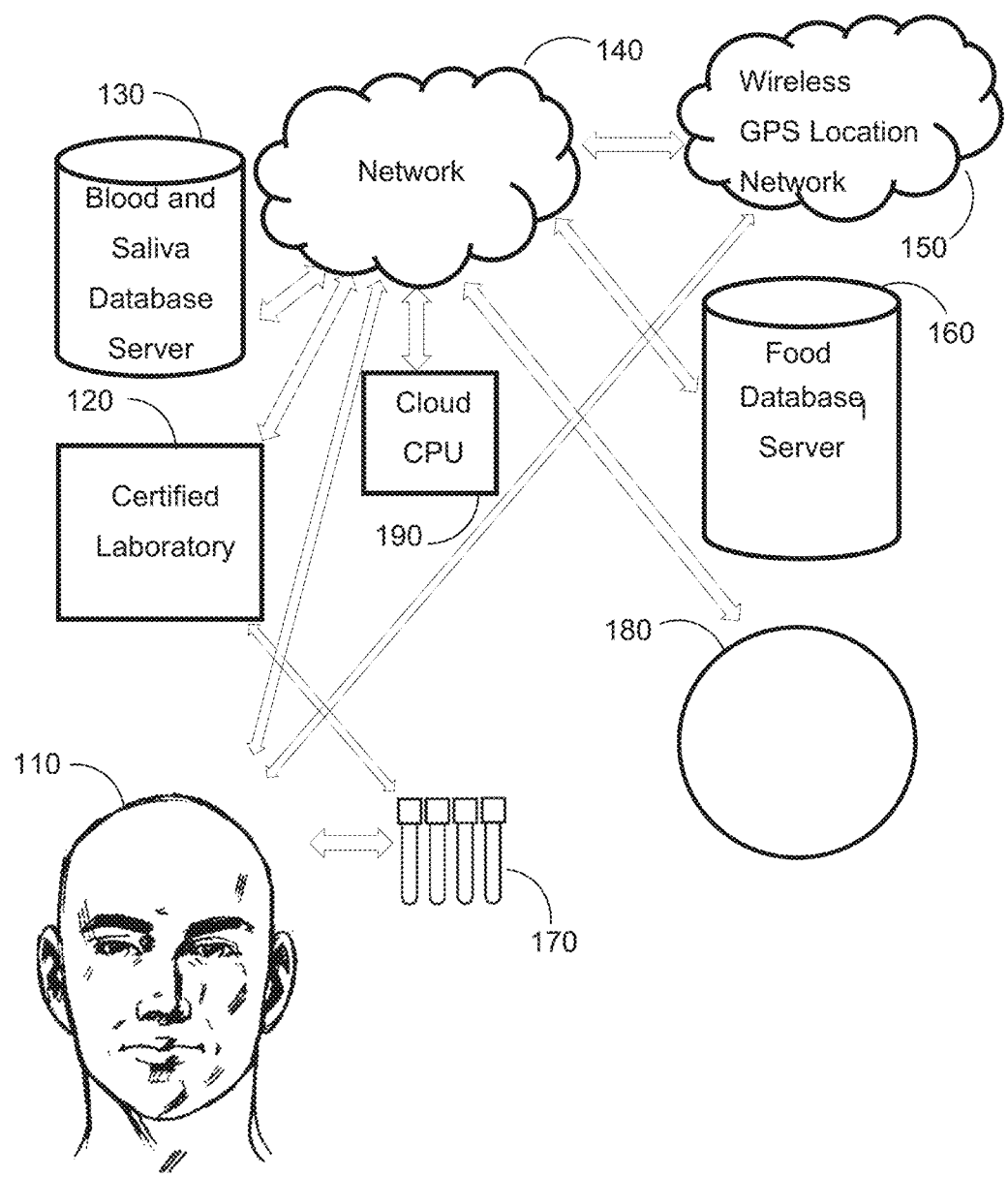
FIG. 1 illustrates a schematic diagram of the network configuration and implementations of methods which support the blood and saliva optimized algorithms for food ordering and consumption in accordance with some embodiments.

The following paragraphs provide a brief summary of various techniques described herein, such as implementations illustrated in FIG. 1. For the purpose of efficiency in this document we will interchangeably use the term "User" and "Foodie". In one implementation as illustrated in FIG. 1, a user 110 may provide a blood and saliva sample 170 to a certified laboratory 120 through a plurality of options. The certified laboratory then transmits the test results from the blood and saliva samples to a network 140 which then archives the data in a blood and saliva database server 130. The network 140 also interacts with the user 110 and a food database server 160, which has compiled a plurality of nutrition information on food ingredients from a plurality of global resources. Food providers of raw food ingredients or prepared dishes use the graphical user interface 180 to upload ingredient information to the network 140, which then stores the nutrition information in the food database server 160. The user 110 interacts with the network 140 through the graphical user interface 180 by selecting a plurality of options regarding nutrition, health, variety, flavoring, style, ethnicity and delivery of prepared and raw ingredients. The cloud based CPU 190 contains algorithms of linear and non-linear equations, which use a plurality of vectors to determine the optimal nutrition ingredients or prepared dishes that optimize the blood and saliva chemistry of the user 110 by interaction with the network 140 and pulling data recursively from the blood and saliva database server 130 and food database server 160. The user 110 may submit blood and saliva samples 170 to the certified laboratory 120 through a plurality of methods to update the network 140 and blood and saliva database server 130 in a plurality of frequencies to improve the ability of the algorithms in the cloud CPU 190 to optimize ingredients from the food database server. The food database server 160 contains a schema for individual ingredients, as well as combinations of ingredients from recipes, which have been uploaded by a plurality of users 110 through the graphical user interface 180. The graphical user interface 180 may be obtained on a stationary CPU, mobile device, augmented reality device, mixed reality device, or any device capable of presenting a graphical user interface 180 to a user 110. The form of the graphical user interface 180 may be a globe with flags of countries, a map with geographic location of countries, country listing, voice listing of countries or other representations of geographic and cultural areas 180. The user 110, network 140, and graphical user interface 180 may interact with the wireless GPS location network 150 to obtain position of the user 110 relative to other users to consider delivery mechanisms to the user 110 and to constrain the optimization equations for cost of delivery.

Figure 2:
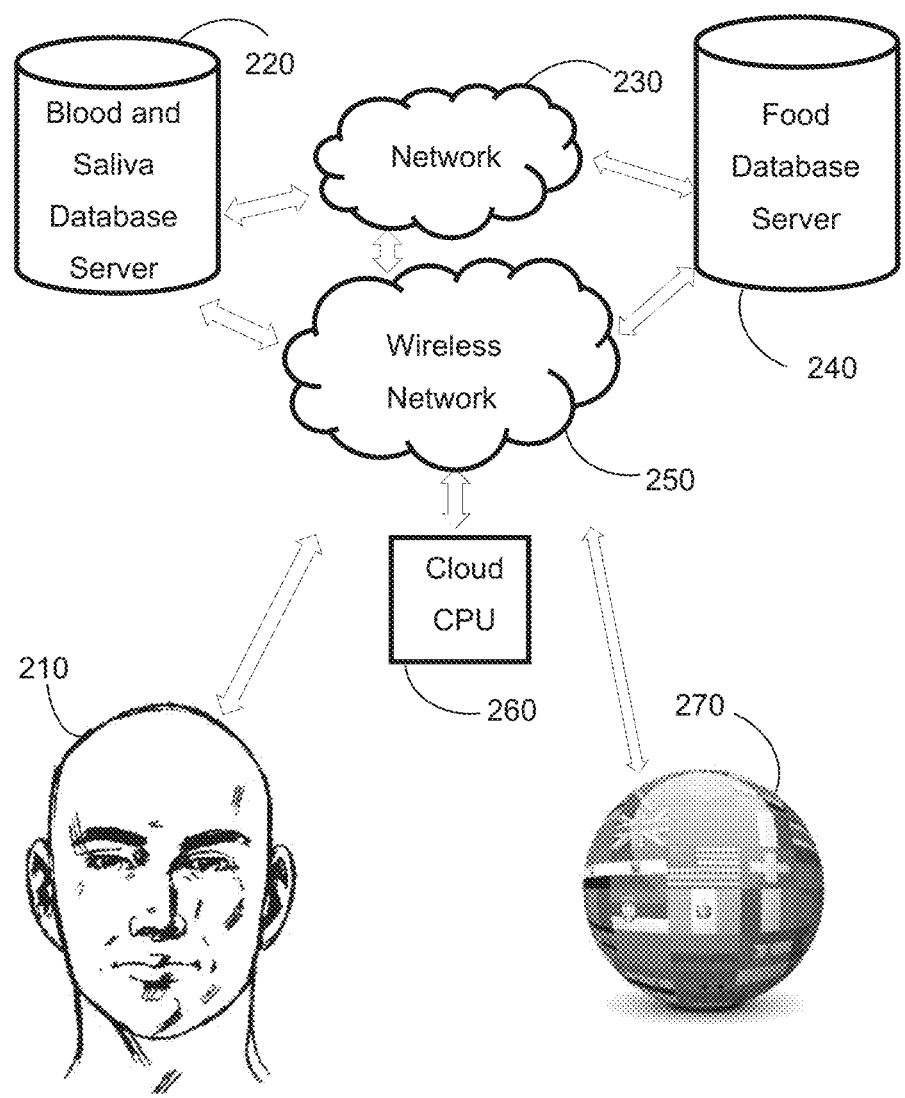
FIG. 2 illustrates a schematic diagram of the network configuration and implementations of methods which support the blood and saliva optimized algorithms for food ordering and consumption and the associated application graphical user interface designed for both 2d and 3d smart devices as well as augmented reality and mixed reality interface configurations in accordance with some embodiments.

The embodiment illustrated in FIG. 2 illustrates further a user 210 interacting with a wireless network 250 and a network 230 that connects a blood and saliva database server 220 based on blood and saliva samples and test results from a user 210 with a food database server 240 containing nutrition data for raw ingredients and combinations of raw ingredients in the form of recipes and prepared food combinations of nutrition, health, variety, flavoring, style, ethnicity and delivery. The user 210 may access the wireless network 250, network 230, blood and saliva database server 220, food database server 240, cloud CPU 260 or other CPUs accessible through the network 230 through the graphical user interface 270. The user 210 continuously updates the blood and saliva database server 220, such as by having a certified laboratory or certified home collection kit collect blood and saliva samples on a plurality of intervals to optimize food selection from the food database server 240.

Figure 3A:
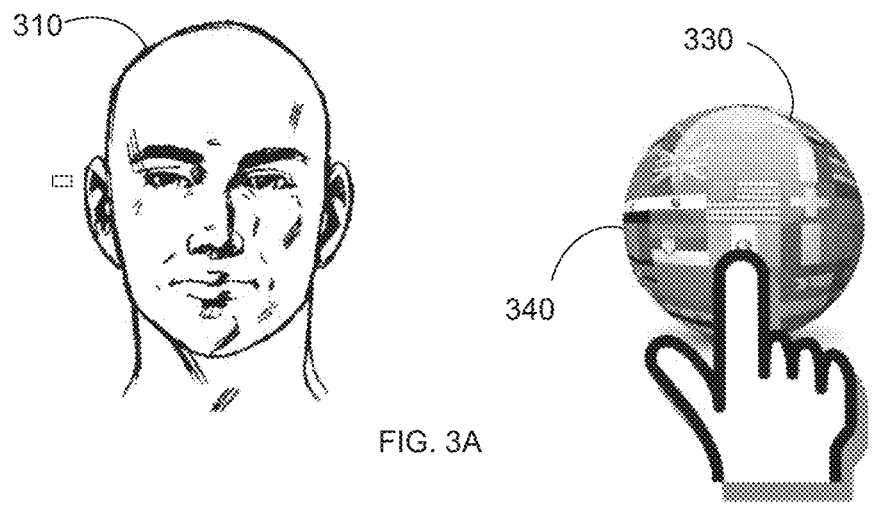
FIGS. 3A and 3B illustrate the implementation of methods of a typical user selecting the ethnicity or style of food prior to the algorithms optimization calculations considering the blood and saliva chemistry of the user amongst other variables in accordance with some embodiments.
Figure 3B:
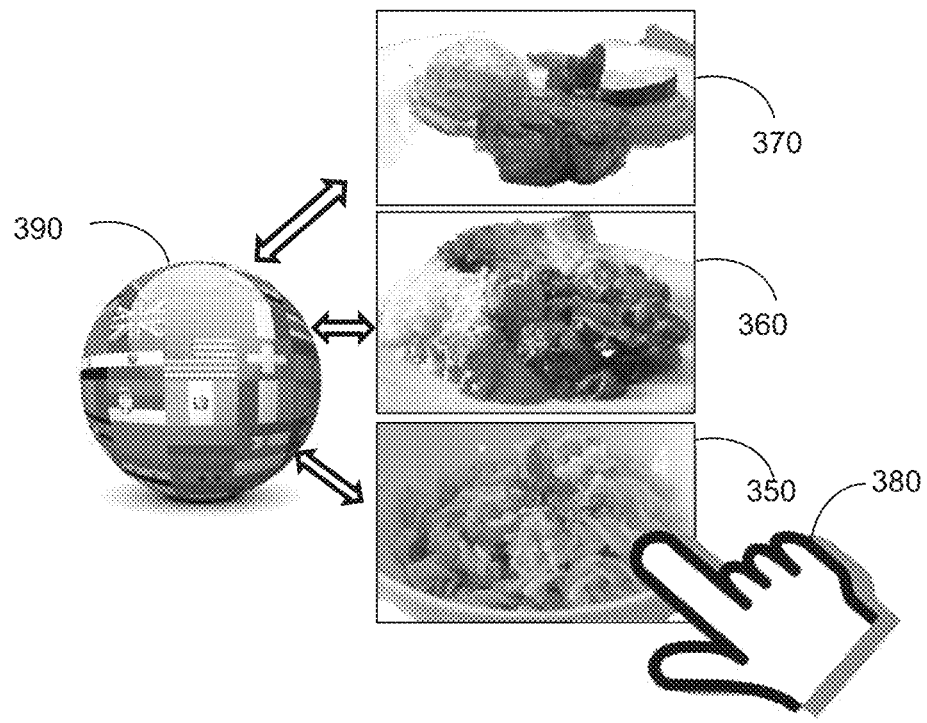

The embodiment illustrated in FIG. 3A illustrates further a user 310 selecting a country of origin for food flavor, variety, style, ethnicity preference from the graphical user interface 330. The user 310 may select the flavor, variety, style, ethnicity preference 340, which then initiates a method of setting up a recursive process of performing optimization equations on linear and nonlinear algebra vectors of various food combinations that optimize the chemistry of blood and saliva. The embodiment illustrated in FIG. 3B illustrates further that a user 310 directs a tool 380 from the graphical user interface 390 to select a plurality of prepared or raw food options, such as a combination of meat, potatoes and other vegetables 370, rice, Indian sauces, breads 360, and seafood pasta 350. The user 310 may scroll the suggested options 370, 360, 350 by sliding, rolling, swiping or other intuitive movements to the graphical user interface 390 user controlled pointer 380.

Figure 4A:
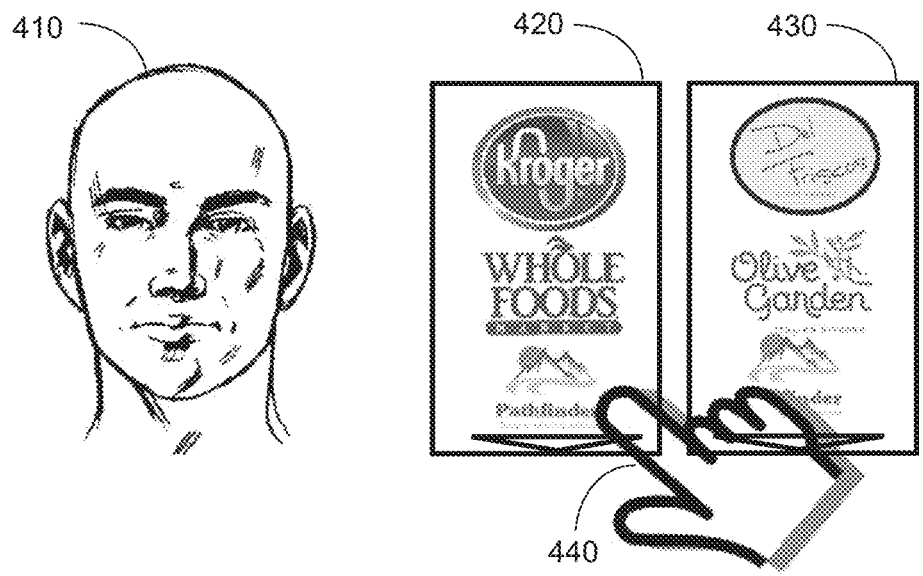
FIGS. 4A and 4B illustrate the implementation of methods of a typical user selecting a plurality of food distributors of prepared or raw food utilizing the graphical user interface of the blood and saliva nutrition optimized algorithms in accordance with some embodiments.
Figure 4B:
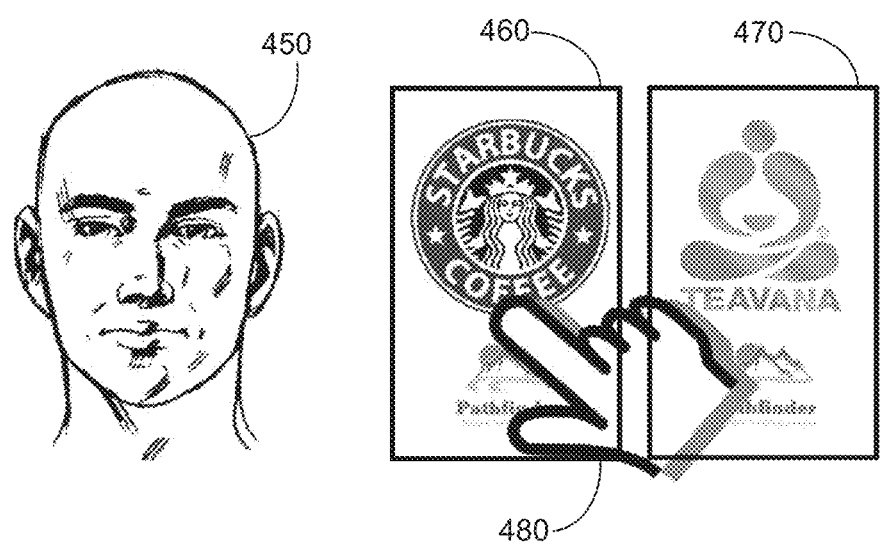

The embodiment illustrated in FIG. 4A illustrates further a user 410 selecting with the graphical user interface pointer 440 a store or brand of food 420 which carries raw food or prepared foods that have been uploaded by the vendor 420 so that the optimization equations may select raw ingredients, combinations of raw ingredients and prepared foods which optimize the user's 410 blood and saliva chemistry. The user 410 may also select restaurants 430 that have uploaded food menus or food choices that have been optimized for the user's 410 blood and saliva chemistry. The embodiment illustrated in FIG. 4B illustrates further a user 450 directing a graphical user interface pointer 480 in one configuration amongst many configurations where the user 450 may select a drink such as coffee, hot chocolate, tea, wine, milk, water, carbonated drink, juice, beer, cider, or spirit from a vendor 460, 470 who participates in the system.

Figure 6A:
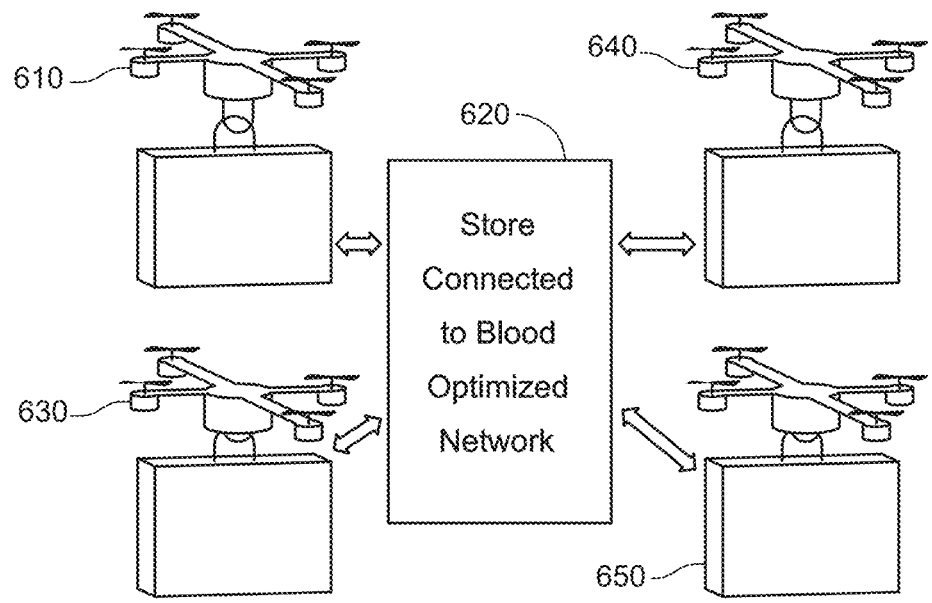
FIGS. 6A and 6B illustrate the implementation of methods of delivery of raw food or prepared food and beverage over the network of stores which are connected to the blood and saliva optimized network in accordance with some embodiments.
Figure 6B:
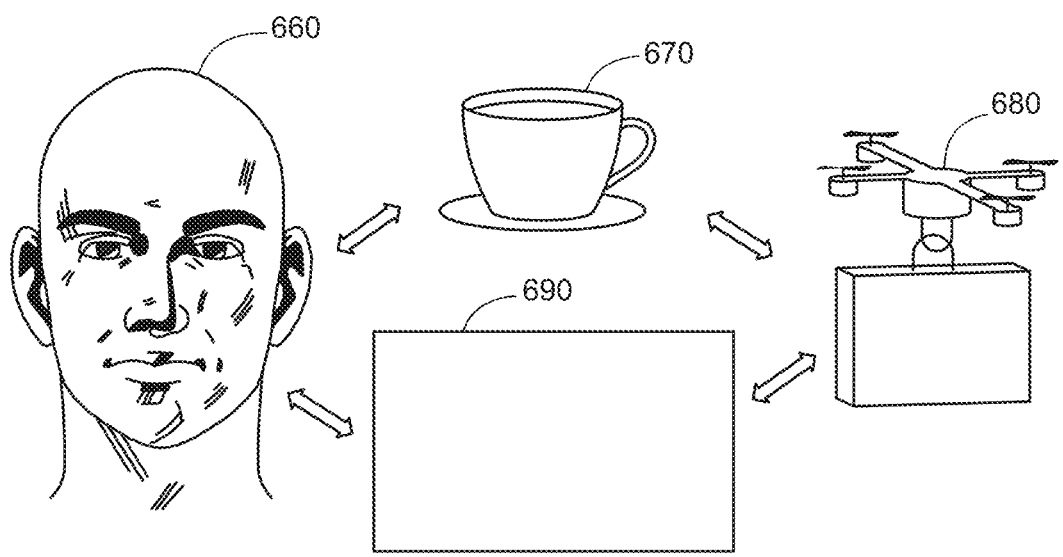

The embodiment illustrated in FIG. 5 illustrates further a user 510 selecting with the graphical user interface pointer 540 a style, country, flavor, or ethnicity of food 530 as an input to the vector based system of linear and non-linear equations to optimize blood and saliva chemistry of a user 510, taking into account the style, country, flavor, or ethnicity that the user 510 desires The embodiment illustrated in FIG. 6B illustrates further a user 660 selecting with the graphical user interface a drink 670 and combination of ingredients in the form of a recipe which includes raw ingredients or prepared food 690, which can then be picked up at a specified location or delivered to the user 660 via a drone 680 or a plurality of other delivery methods. The embodiment illustrated in FIG. 6A illustrates further a user 660 that may be connected to the network of stores that use the blood and saliva optimized database structure and schema 620 to optimize blood and saliva chemistry while considering food consumption. A plurality of pick up or delivery methods may be utilized that include, but are not limited to, programmed drones 610, 630, 640, 650. The drones 680 may be operated by humans or may be autonomous.

Figure 7A:
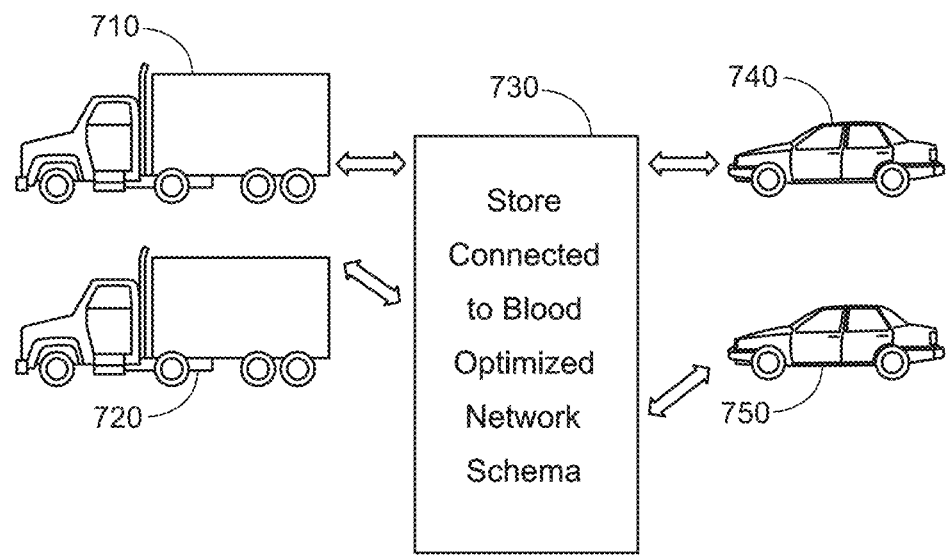
FIGS. 7A and 7B illustrate the implementation of methods of delivery of raw food or prepared food and beverage over the network of stores which are connected to the blood and saliva optimized network in accordance with some embodiments.
Figure 7B:
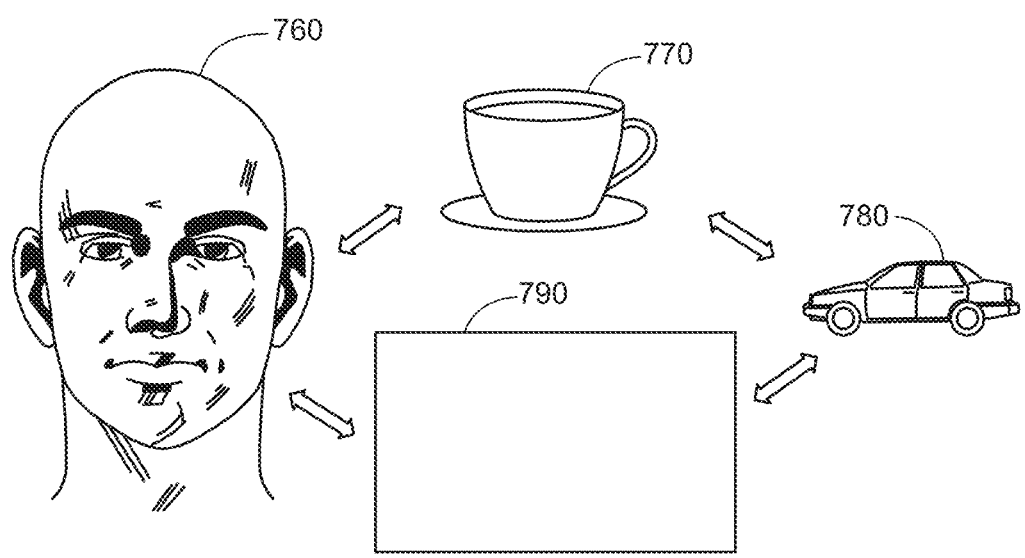

The embodiment illustrated in FIG. 7B illustrates further a user 760 selecting with the graphical user interface a drink 770 and combination of ingredients in the form of a recipe which includes raw ingredients or prepared food 790, which can then be picked up at a specified location or delivered to the user 760 via a vehicle 780 or a plurality of other delivery methods. The embodiment illustrated in FIG. 7A illustrates further a user 760 that may be connected to the network of stores that use the blood and saliva optimized database structure and schema 730 to optimize blood and saliva chemistry while considering food consumption. A plurality of pick up or delivery methods may be utilized that include but are not limited to programmed vehicles 710, 720, 740, 750. The vehicles 780 may be operated by humans or may be autonomous.

Figure 8:
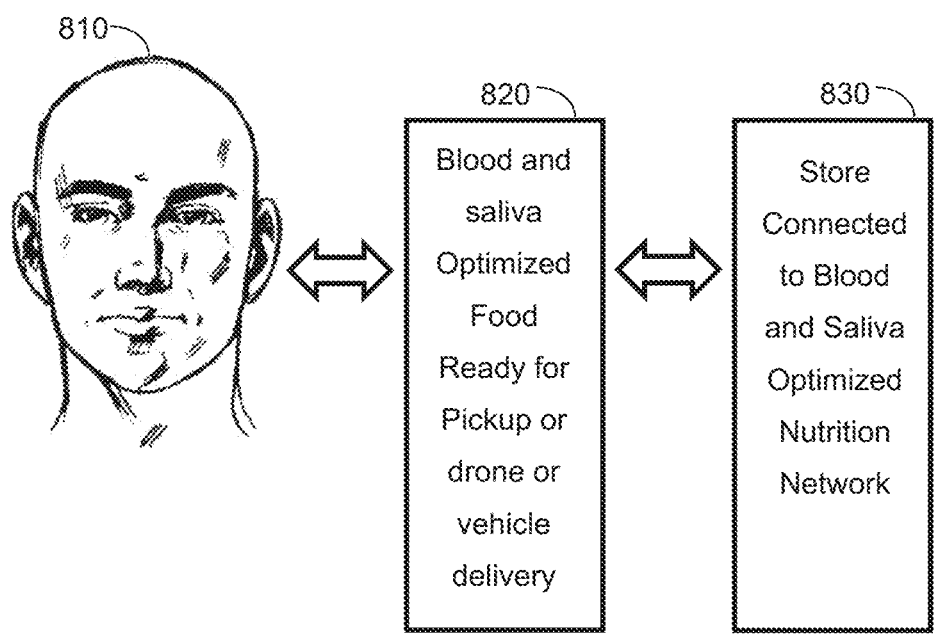
FIG. 8 illustrates the implementation of methods of delivery of raw food or prepared food and beverage over the network of stores which are connected to the blood and saliva optimized network in accordance with some embodiments.

The embodiment illustrated in FIG. 8 illustrates further that a user 810 may select, with the graphical user interface, blood and saliva optimized food which is ready for pickup 820 from a store, restaurant, or cooking node that is connected to the blood and saliva optimized network 830. Grocery stores, food warehouses, co-ops, food distribution centers, restaurants, certified kitchens, or a plurality of other nodes capable of providing raw or prepared food may be connected to the blood and saliva optimized nutrition network 830. Grocery stores, food warehouses, co-ops, food distribution centers, restaurants, certified kitchens, or a plurality of other nodes capable of providing raw or prepared food may prepare the food for pickup 820 or distribute the food via drone or delivery vehicle.

Figure 9:
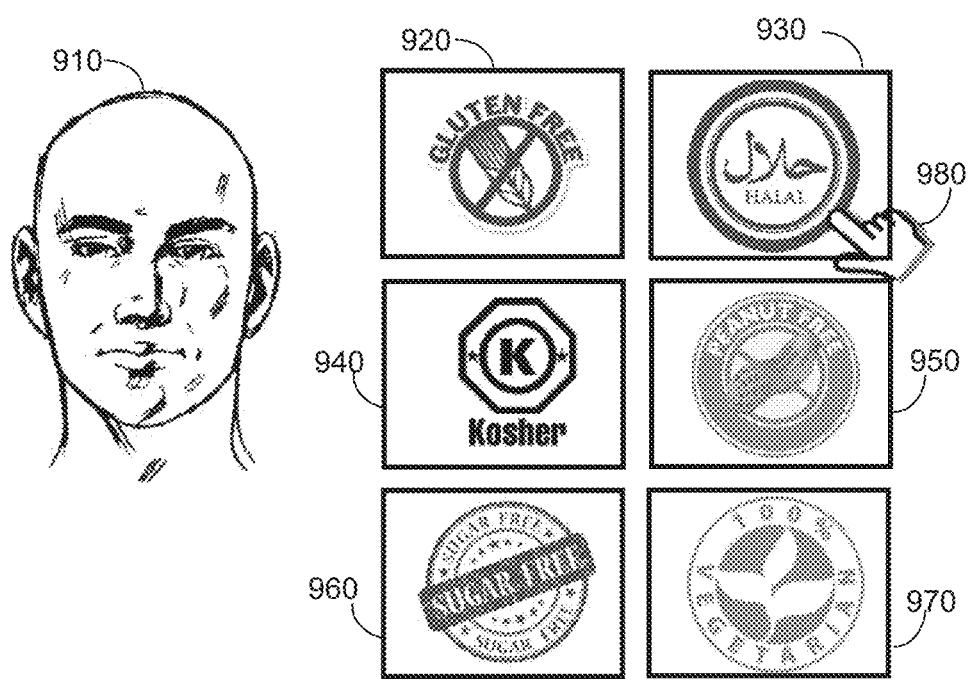
FIG. 9 illustrates the implementation of methods dietary type of style choices in the delivery matrix of raw food or prepared food and beverage over the network of stores which are connected to the blood and saliva optimized network in accordance with some embodiments.

The embodiment illustrated in FIG. 9 illustrates further that a user 910 may select, with the graphical user interface pointer 980, blood and saliva optimized food that may have a certain type of food designation such as gluten free 920, halal 930, kosher 940, peanut free 950, sugar free 960, vegetarian 970, or a plurality of other designations that would be in the preference portfolio vector of the user 910.

In one implementation as illustrated in FIG. 10, the system may provide a blood and saliva sample 170 to a certified laboratory 120 through a plurality of options.

Figure 11:
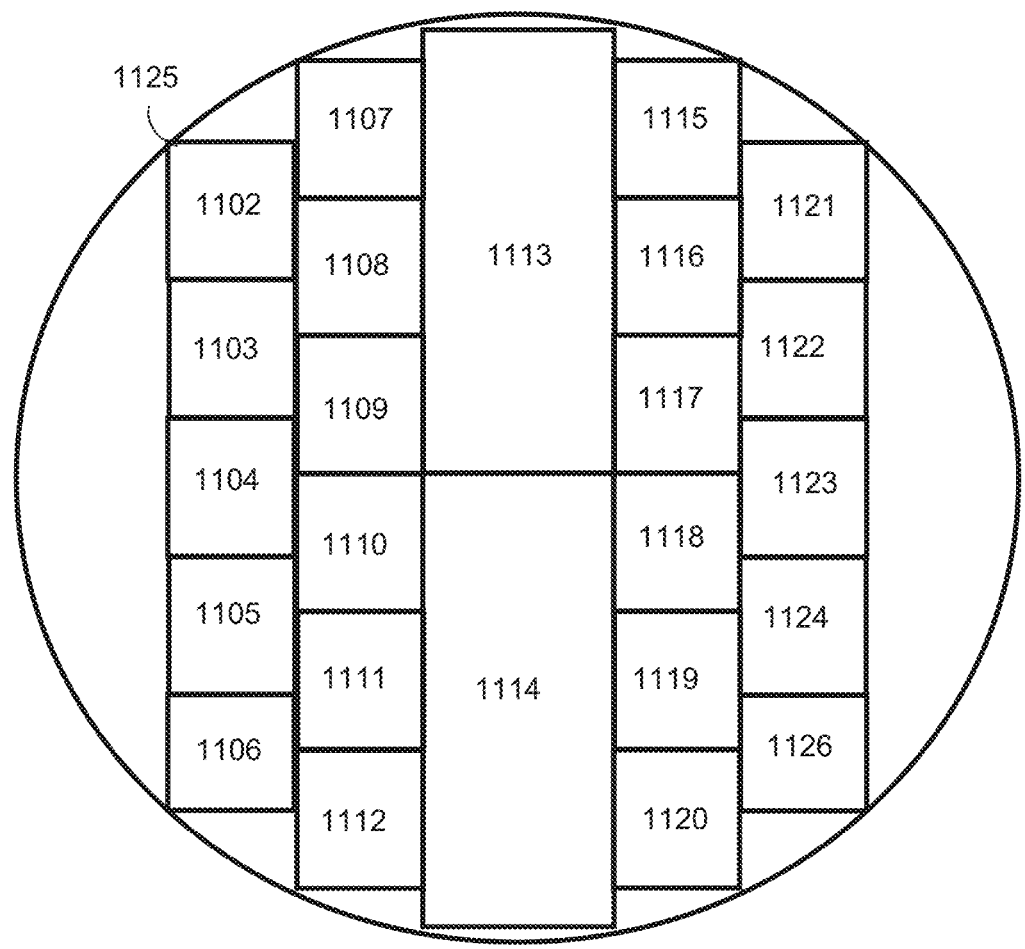
FIG. 11 illustrates a diagram of the mobile computer ball device in accordance with some embodiments.

The embodiment illustrated in FIG. 11 illustrates the mobile network based ball CPU projection device 1125. The blood and saliva optimized food methods and system may be used on any CPU device which is stationary or mobile with access to a network. One configuration of a CPU device which can process the blood and saliva optimized food methods and system may be the device 1125 which may include a memory 1102, a memory controller 1103, one or more processing units (CPUs) 1104, a peripherals interface 1105, RF circuitry 1106, audio circuitry 1108, one or more speakers 1107 and 1115, a microphone 1109, an input/output (I/O) subsystem 1110, input control devices 1111, an external port 1112, optical sensors 1116, camera 1113, one or more laser projection systems 1114, power supply 1117, battery 1118, wifi module 1119, GPS receiver 1120, accelerometer 1121, ambient light sensor 1122, location sensor 1123, barometer 1124, and USB port 1126. The device 1125 may include more or fewer components or may have a different configuration or arrangement of components. The CPUs 1104 run or execute various instructions compiled by software and applications, which are stored in the memory 1102, that perform various functions on the device 1125, such as the blood and saliva optimized food methods and system. The RF circuitry 1106 receives and sends RF signals. The RF circuitry 1106 converts electrical signals to/from electromagnetic signals and communicates with communications networks 140 and 150 and other communication devices via the electromagnetic signals. The instructions to perform the mathematic algorithm optimization may be on a local CPU such as 1104 or a cloud based CPU 190. The RF circuitry may be comprised of, but not limited to, an antenna system, a tuner, a digital signal processor, an analogue signal processor, various CODECs, a SIM card, memory, amplifiers, an oscillator and a transceiver. The wireless communication components may use a plurality of standard industry protocols, such as Global System for Mobile Communication ("GSM"), Voice over internet protocol ("VOIP"), long-term evolution ("LTE"), code division multiple access ("CDMA"), Wireless Fidelity ("WiFi"), Bluetooth, Post office Protocol ("POP"), instant messaging, Enhanced Data GSM Environment ("EDGE"), short message service ("SMS"), or other communication protocol invented or not yet invented as of the filing or publish date of this document. The input/output subsystem 1110 couples with input/output peripherals 1105, other control devices 1111, and other laser projection systems 1114 to control the device 1125. The laser projection system 1114 and camera 1113 take infrared tracking information feedback from the user 110 into the peripheral interface 1105 and CPU 1104 to combine the data with instructions in the CPU 1104 and memory 1102 that provide an iterative instruction for the graphical user interface after comparison with information in the memory from the database server 130. The input control devices 1111 may be controlled by user 110 movements that are recorded by the laser projection system 1114 and camera 1113. The audio circuitry 1108, one or more first speakers 1107, one or more second speakers 1115, and the microphone 1119 provide an audio interface between the user and the device 1125. The audio circuitry 1108 receives audio data from the peripherals interface 1105, converts the data to an electrical signal, and transmits the electrical signal to the speakers 1107 and 1115. The speakers 1107 and 1115 convert the electrical signals to human audible sound waves which are mechanotransducted into electrical impulses along auditory nerve fibers and further processed into the brain as neural signals. The audio circuitry 1108 also receives electrical signals converted by the microphone 1109 from sound waves. The audio circuitry 1108 converts the electrical signal to audio data and transmits the audio data to the peripherals interface 1105 for processing. Audio data may be retrieved and/or transmitted to memory 1102 and/or the RF circuitry 1106 by the peripherals interface 1105. In some embodiments the RF circuitry 1106 may produce ultra-high frequency waves that are transmitted to wireless headphones, which then convert the electrical signals to human audible sound waves which are mechanotransducted into electrical impulses along auditory nerve fibers and further processed into the brain as neural signals. The device 1125 also includes a power supply 1117 and battery 1118 for powering the various components. The USB port 1126 may be used for providing power to the battery 1118 for storage of power. The location sensor 1123 couples with the peripherals interface 1105 or input/output subsystem 1110 to disable the device if the device 1125 is placed in a pocket, purse or other dark area to prevent unnecessary power loss when the device 1125 is not being used. The software instructions stored in the memory 1102 may include an operating system (LINUX, OS X, WINDOWS, UNIX, or a proprietary operating system) of instructions of various graphical user interfaces.

Figure 12:
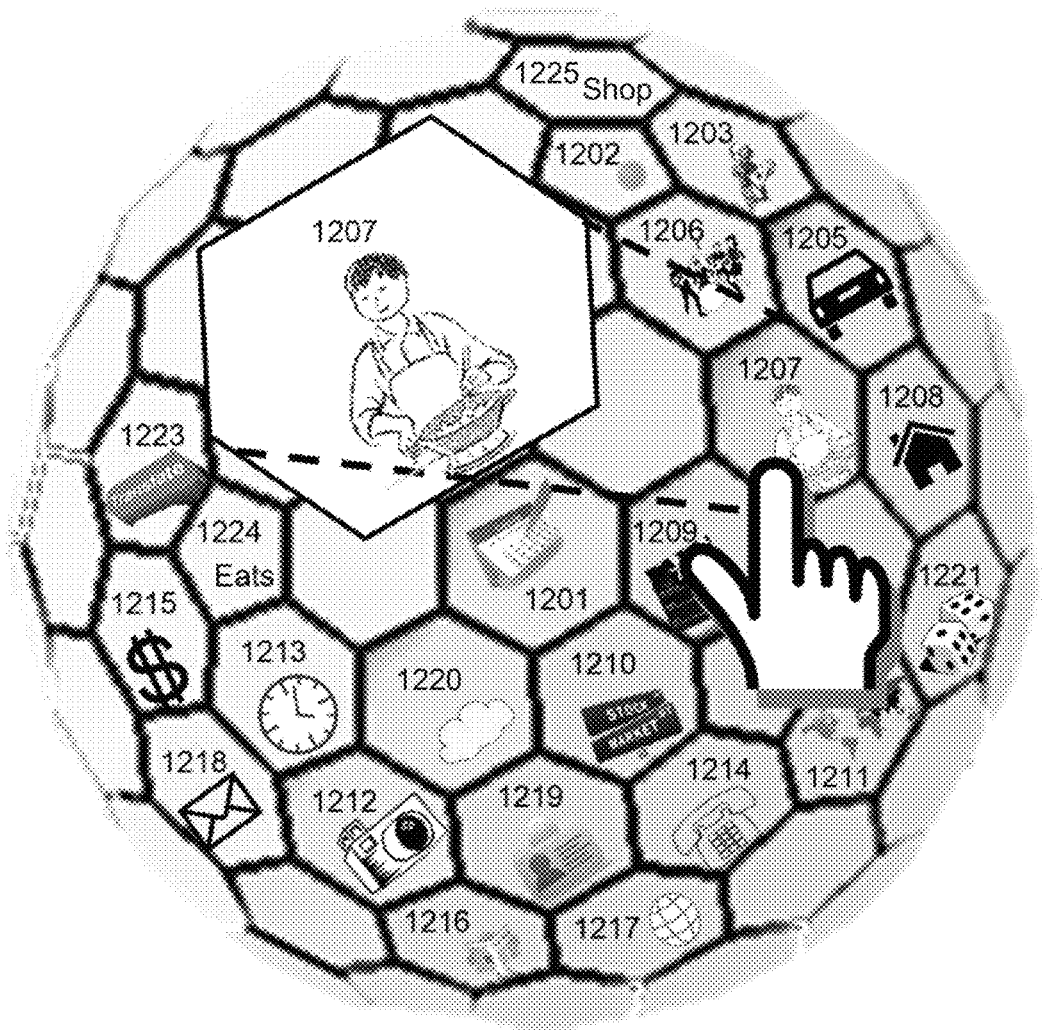
FIG. 12 illustrates an exemplary user interface for selecting a plurality of applications in accordance with some embodiments.

The embodiment illustrated in FIG. 12 illustrates the graphical user interface of the system which may include a network based ball CPU projection device 1125. The system may include instructions for object hologram embodiments of a calendar 1201, photos, camera 1212, videos 1209, maps 1211, weather 1202, credit cards, banking 1215, cryptocurrency, notes, clocks 1213, music 1206, application hosting servers 1220, settings, physical fitness 1203, news 1216, video conferencing, home security 1208, home lighting, home watering systems, home energy or temperature settings, home cooking 1207, phone 1214, texting services, mail 1218, internet 1217, social networking, blogs, investments 1210, books, television, movies, device location, flashlights, music tuners, airlines, transportation 1205, identification 1219, translation, gaming 1221, real estate, shopping, food, commodities 1215, technology, memberships, applications, web applications, audio media, visual media, mapping or GPS, touch media, general communication, internet, mail 1218, contacts, cloud services, games, translation services 1223, virtual drive through with geofence location services for nearby restaurants to allow advance ordering of food and payment 1224, such as the food and saliva based algorithm to optimize personal nutrition, virtual shopping with custom measurements through infrared scans 1225, etc., and facilitates communication between various hardware and software components. The blood and saliva optimized food algorithm application may appear as represented in object 1207 or 1224. The application 1207 or 1224 may scan pictures of food which has been set for consumption by the user and which has not been ordered through the system so that the ingredients may be identified and the data included in the blood and saliva based optimization models of blood and saliva chemistry.

Figure 13:
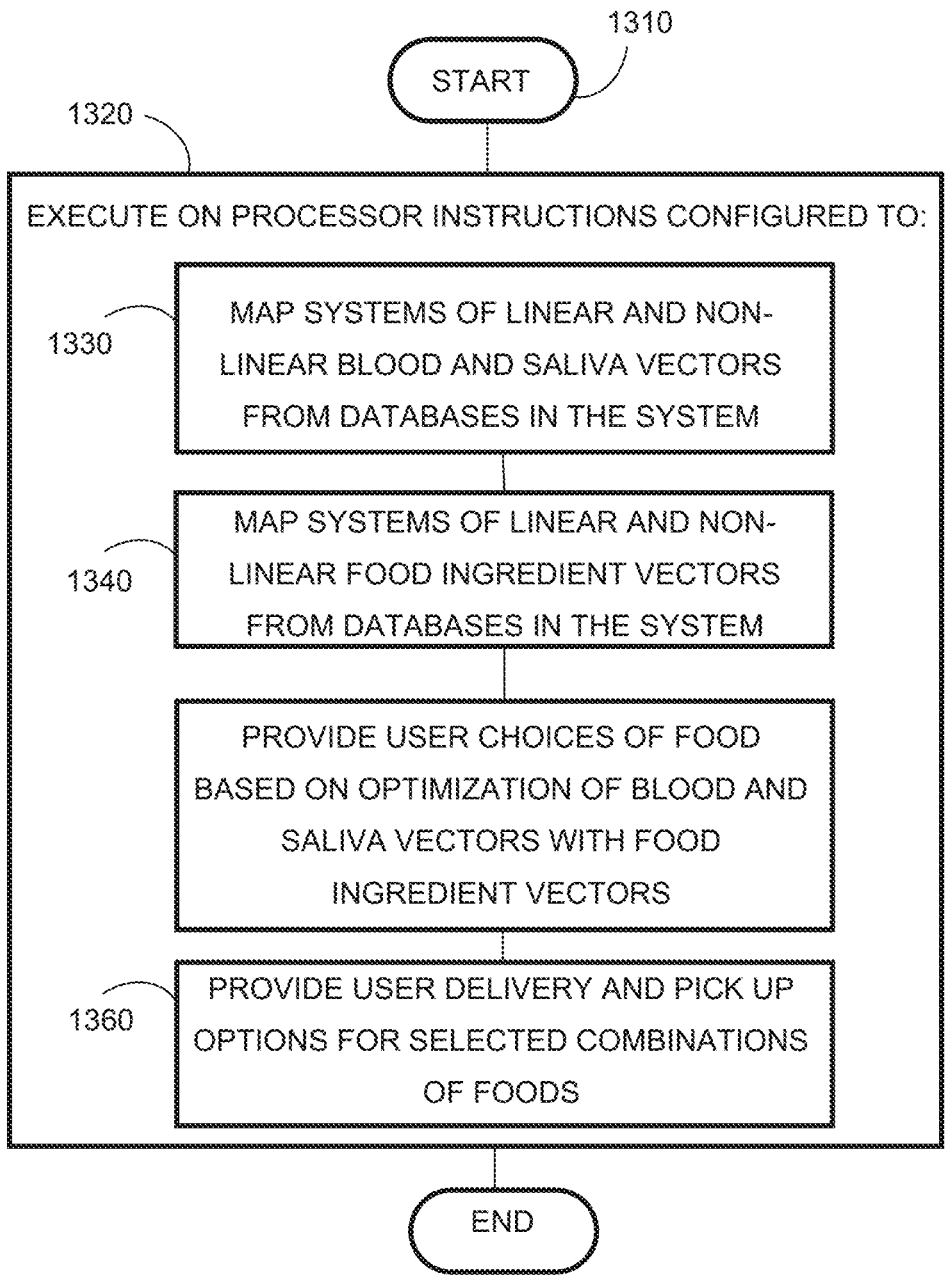
FIG. 13 illustrates an exemplary flow chart of a plurality of applications and iterations of the blood and saliva chemistry of a user through linear and non-linear vector maximization and minimization equations in accordance with some embodiments in accordance with some embodiments.

The process flow diagram in FIG. 13 illustrates implementations of methods and the system where a user uses the system and methods. A user starts 1310 the implementation of the methods and systems by selecting a plurality of options regarding nutrition, health, variety, flavoring, style, ethnicity and delivery. The system takes the inputs to execute on a processor instructions configured to 1320 complete the following instructions. In one implementation of the methods, the system maps systems of linear and non-linear blood and saliva vectors from databases in the system 1330. The map of the system of linear and non-linear blood and saliva vectors forms a matrix which will then form the basis of part of the system of optimization equations used to select food options for the user. The system and methods further map systems of linear and non-linear food ingredient vectors from databases in the system 1340 which form a matrix of food nutrition content. The matrices are then multiplied to optimize the weights of ingredients to ensure optimal blood and saliva chemistry for the user's body. The variance-covariance matrix is square and symmetric. The optimization equation weights have also considered groups of food ingredients that form the basis of prepared meals and recipes which are combinations of ingredients. The system then provides the user delivery and pick-up options for selected combinations of foods 1360. The implementation of methods is recursive and the optimal weights are being adjusted after each meal considering the historical ingredients consumed and blood and saliva sampling data that is submitted into the database of the system. The techniques and methods discussed herein may be devised with variations in many respects, and some variations may present additional advantages and/or reduce disadvantages with respect to other variations of these and other techniques and methods. Moreover, some variations may be implemented in combination, and some combinations may feature additional advantages and/or reduced disadvantages through synergistic cooperation and reweighting of the models through recursive optimization. The variations may be incorporated in various embodiments to confer individual and/or synergistic advantages upon such embodiments.

The embodiment of the method and system illustrated in FIGS. 14A, 14B, 14C, and 14D illustrate a representative food market with heterogeneous expectations. Traditionally, the buyer and seller have very different information. In an exemplary scenario, the seller, manufacturer, or cook knows the ingredient attributes, whereas the buyer may make a purchase without knowing the ingredient attributes or their chemistry effect on the blood. Surely, the buyer can do research on all of the ingredients, but generally the buyer does not have the same resources as the producer of the food, who has food scientists and research staff to understand the effects of the ingredient attributes on blood chemistry or other aspects of human health. Similarly, a mother or father may make a batch of cookies for their child, thinking that the act of making cookies is showing love to their child if consumed in reasonable quantities. However, if the father or mother did not know their child was gluten intolerant or had celiac disease, then, in fact, they were unknowingly inflicting pain on their child through the dietary choice. The implementation of the method considers that it is very costly for buyers and sellers of food to have homogeneous information, or even to reduce heterogeneous information, so that people make less sub-optimal food choices as consumers or that stores offer the wrong types of food to their primary demographics and customers. The implementation of the method has provided a solution for these problems and has greatly reduced or nearly eliminated the problem of heterogeneous information on food ingredients relative to personal blood chemistry and saliva chemistry. The implementation of the method allows both the restaurant and the customer to speak the same language of food chemistry for the respective blood and saliva chemistry while considering flavor, ethnicity, or style preferences. The implementation of the method allows both the grocery store and the customer to speak the same language of food chemistry for the respective blood and saliva chemistry while considering flavor, ethnicity, or style preferences. The implementation of the method allows both the family meal cook and the family member or friend to speak the same language of food chemistry for the respective blood and saliva chemistry while considering flavor, ethnicity, or style preferences. The implementation of the method allows both host of a party and all the guests to speak the same language of food chemistry for the respective blood and saliva chemistry of guests while considering flavor, ethnicity, or style preferences. Blood tests and saliva historically have been costly, which adds to the problem of heterogeneous information between food provider and food consumer. The implementation of the method and system covers the cost of the blood and saliva test, which can be self-administered with system equipment or administered by a lab in the system and method network. The method and system may reduce the overall food consumption of the user by providing mathematically rigorous and nutritional foods for the consumer's blood, which reduces food waste and wasted calorie consumption. The blood and saliva test may be self-administered through method and system equipment that is sent to the user or administered by a lab in the system. To quantify embodiments of the method and system, FIG. 14A illustrates a general utility function. The system and method assigns a utility function or "Foodie Score" 1410 to their diet preferences, which ranks through a series of neural network feedback on food styles, ethnicity, variety, and flavoring. The equation 1410 has the following variables: F(foodie score), which is the utility function, and E(Bblood chemistry), which is the current blood chemistry of a portfolio of ingredients minus 0.005, which is a scaling convention that allows the system and method to express the current blood chemistry of a portfolio of ingredients and the standard deviation of those ingredients to be a percentage rather than a decimal. The term A in 1410 is an index of the user's preference which is derived from using neural networks that have been trained on the users preferences. The term A in 1410 is continually updated in a recursive fashion to reflect the user's preferences in style, ethnicity, flavoring or other characteristics. The sigma term squared in 1410 is the variance of the blood chemistry of a portfolio of ingredients. The utility function or foodie score represents the notion that the foodie utility is enhanced or goes up when the blood chemistry is within target, and diminished or reduced by high variance blood chemistry or blood chemistry which brings the user out of target ranges. The extent by which the foodie or user is negatively affected by blood chemistry variance or blood chemistry outside of target ranges depends on the term A in 1410, which is the user's preference index. More dietary sensitive foodies or users may have a higher term A index value, as their blood chemistry is disadvantaged more by blood chemistry variance and out of range blood chemistry. A Foodie or user may pick meals or portfolios of ingredients based on the highest F(foodie score) in the equation in 1410. If a food ingredient or portfolio of ingredients has no variance to blood chemistry of the user, then a selection will have a utility or Foodie Score of the expected blood chemistry without variance as the sigma term in the equation in 1410 is equal to zero. The equation in 1410 provides a benchmark for the system and method to evaluate a meal's effect on blood chemistry. In the implementation of the method according to the equation in 1410, the term A determines preferences of the user, which then may cause a certain meal to be accepted or rejected based upon the effect to blood chemistry.

The implementation of the system and method is further represented in 1420 to take a simple two state case of blood chemistry for an exemplary user. If a user has an initial blood chemistry represented as a vector of attributes, and assume two possible results after eating an ingredient or a portfolio of ingredients as a meal with a vector of blood chemistry attributes, then probability of state one is p for state of Blood Chemistry 1 and a probability for the state two of blood chemistry 2 is (1-p). Accordingly, the expected value of blood chemistry, as illustrated in the set of equations in 1430, is E(Bblood chemistry) equals probability p multiplied by blood chemistry state 1 plus probability (1-p) multiplied by blood chemistry state 2. The variance or sigma squared of the blood chemistry is represented in 1440.

Figures 15A, 15B:
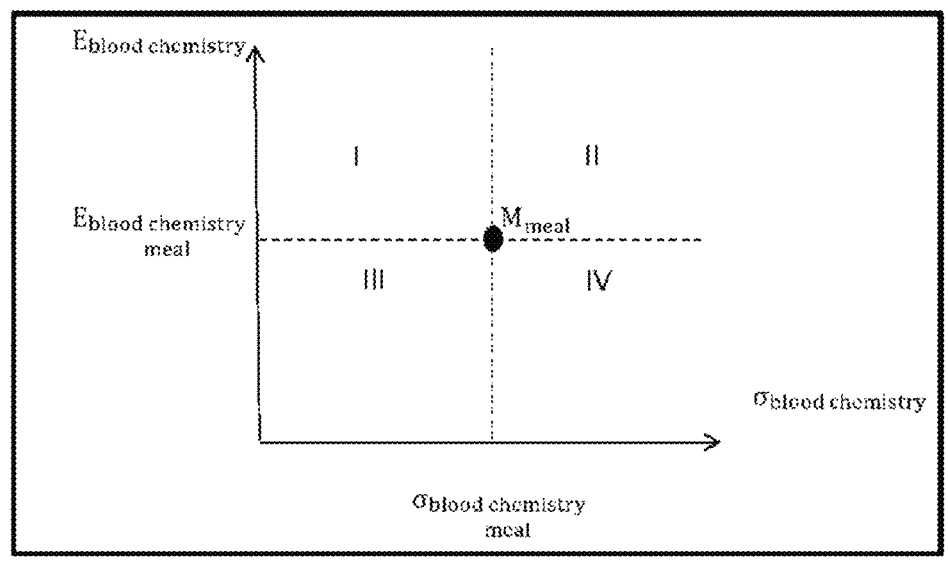
FIGS. 15A and 15B illustrate the embodiment of the method and system in FIG. 15A representing the tradeoff between the standard deviation of blood chemistry of a meal and the expected return of the blood chemistry of a meal while 15B represents the inequality condition.

The embodiment of the method and system in FIG. 15A represents the tradeoff between the standard deviation of blood chemistry of a meal and the expected return of the blood chemistry of a meal. Meal $M_{meal}$ is preferred by Foodies with a high term A index value to any alternative meal in quadrant IV, because the expected value of the blood chemistry of the meal is expected to be equal to or greater than any meal in quadrant IV and a standard deviation of the meal blood chemistry is smaller than any meal in that quadrant. Conversely, any meal $M_{meal}$ in quadrant I is preferable to meal $M_{meal}$ because its expected blood chemistry is higher than or equal to $M_{meal}$ and the standard deviation of the blood chemistry of the meal M is equal to or smaller than meal $M_{meal}$. FIG. 15B represents the inequality condition. Accordingly, if the expected value of the blood chemistry of a certain meal 1 is greater than or equal to the expected value of the blood chemistry of a certain meal 2 in 1520, and the standard deviation of the blood chemistry of a certain meal 1 is less than or equal to the standard deviation of the blood chemistry of a certain meal 2 in 1520, then at least one inequality is strict which rules out inequality.

Figures 16A, 16B:
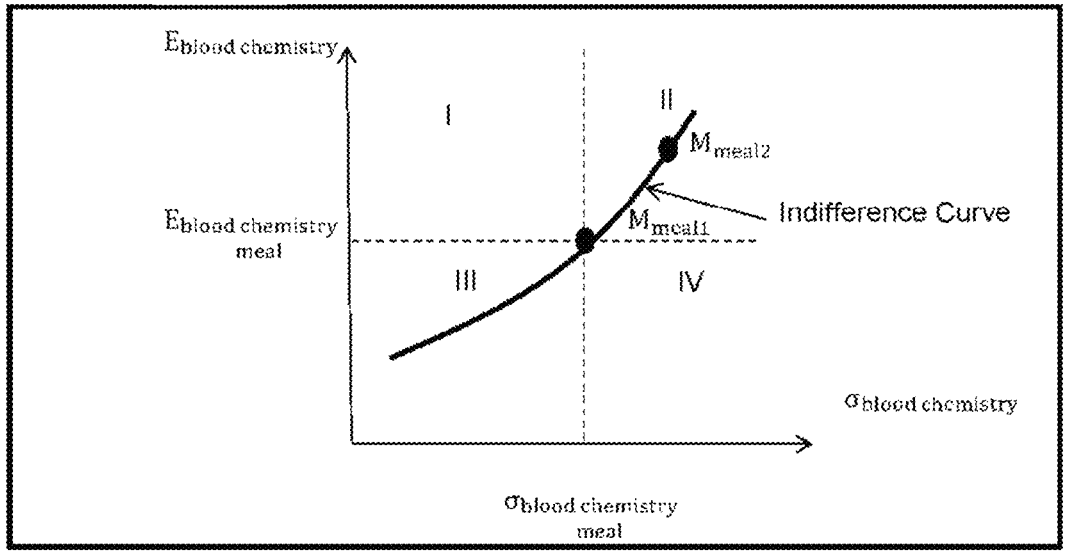
FIG. 16A in the form of a graph and 16B in the form of a table illustrates the points along a Foodies indifference curve where meals have equal utility to the user or Foodie.

The embodiment of the method and system in FIG. 16A supposes a Foodie identifies all the meals that are equally attractive from a utility and blood chemistry perspective to meal $M_{meal2}$, starting at point meal $M_{meal1}$, an increase in standard deviation of the blood chemistry of the meal lowers utility and must be compensated for by an increase in the expected value of the blood chemistry. Thus meal $M_{meal2}$ is equally desirable to the Foodie as meal $M_{meal1}$ along the indifference curve. Foodies are equally attracted to meals with higher expected value of blood chemistry and higher standard deviation of blood chemistry as compared to meals with lower expected value of blood chemistry and lower standard deviation of blood chemistry along the indifference curve. Equally desirable meals lie on the indifference meal curve that connects all meals with the same utility value.

The embodiment of the method and system in FIG. 16B examines meals along a Foodie's indifference curve with utility values of several possible meals for a Foodie with a term A index value of 4, as shown in table 1620. The table of combinations of meals 1620 illustrates as one embodiment an expected value of blood chemistry of a meal index of 10 and a standard deviation of the blood chemistry of the meal of 20%. Accordingly the Foodie Score or utility function is therefore 10 minus 0.005 multiplied by 4 multiplied by 400, which equals 2 as a utility score. FIG. 16B also illustrates 3 additional examples of various expected values of meal blood chemistry and standard deviation of a meals blood chemistry.

FIG. 14A, FIG. 14B, FIG. 15A, FIG. 15B, FIG. 16A, and FIG. 16B discuss the blood chemistry of a meal for a particular Foodie. Such meals are composed of various types of ingredients. Foodies may eat single ingredients or meals which combine ingredients. In some embodiments, adding a certain ingredient increases the utility of a Foodie's blood chemistry, while in some embodiments adding an ingredient decreases the utility. In many contexts, "Health Food" offsets the effects of "Unhealthy Food". In one embodiment, dark chocolate is a power source of antioxidants which raises the utility of the blood chemistry. Chocolate may raise HDL cholesterol and protect LDL Cholesterol against oxidization. Too much chocolate lowers the utility of blood chemistry as it is high in saturated fat and sugar. Excessive sugar spikes the blood glucose chemistry which contributes to calories that do not have much nutrient value for the blood chemistry utility function, which puts as risk weight gain and other health complications. In one implementation of the method and system, a Foodie may think it is counterintuitive adding a seemingly indulgent ingredient or recipe that may actually increase the blood chemistry performance, as it can reduce the build-up of unwanted attributes and reduce the risk or standard deviation of the Foodie's blood chemistry towards an unwanted outcome. Although chocolate in and of itself may have an uncertain outcome and a negative effect on blood chemistry, chocolate combined with other ingredients and recipes may have an overall benefit towards blood chemistry. The helpful effects come from a negative correlation of individual ingredients. The negative correlation has the effect of smoothing blood chemistry for a certain Foodie user.

The embodiment of the method and system in FIG. 17A examines one exemplary probability distribution of a particular ingredient affecting the blood chemistry of a Foodie or user. State 1 probability of the rapini ingredient is 0.5 in table 1710, and the expected value of the rapini ingredient is to increase the blood chemistry by 25% towards the target blood chemistry range. State 2 probability of the rapini ingredient is 0.3 in table 1710 and the expected value of the rapini ingredient is to increase the blood chemistry by 10% towards the target blood chemistry range. State 3 probability of the rapini ingredient is 0.2 in table 1710 and the expected value of the rapini ingredient is to decrease the blood chemistry by 25% towards the target blood chemistry range. Accordingly the effect on the Foodie's blood chemistry is the mean or expected return on blood chemistry of the ingredient, which is a probability weighted average of expected return on blood chemistry in all scenarios, as shown in 1720. Calling Pr(s) the probability scenario s and r(s) the blood chemistry return in scenario s, we may write the expected return E(r) of the ingredient on blood chemistry, as is done in 1720. In FIG. 17B applying the formula of expected return of rapini on blood chemistry with the three possible scenarios in 1710, the expected return of rapini on blood chemistry of the Foodie is 10.5% toward the target range in the example in 1720. The embodiment of the method and system in FIG. 17C illustrates the variance and standard deviation of rapini on blood chemistry is 357.25 for variance and 18.99% for standard deviation, shown in 1730.

Exemplary embodiments of scenario probabilities vary amongst blood types and composites, so the method and system is not limited to a single set of weights, but rather the system learns new weights using neural network probability weightings with iterative feedback from blood sampling to ascertain recursive effects of food chemistry onto blood chemistry.

In an exemplary embodiment in FIG. 18A, the blood chemistry of a vector of ingredients is the weighted average of the blood chemistry of each individual ingredient, so the expected value of the blood chemistry of the meal is the weighted average of the blood chemistry of each individual ingredient, as represented in 1810. In the exemplary two ingredient combination of rapini and chocolate in 1810, the expected value of the combined blood chemistry is 7.75% toward the target blood chemistry range. The weight of an ingredient may be represented to incorporate serving size and calorie count as part of the measure of how ingredients affect blood chemistry.

In an exemplary embodiment in FIG. 18B, the standard deviation of the blood chemistry of the combined ingredients is represented in 1820.

Because the variance is reduced in the combination since the foods were not perfectly correlated, the exemplary implementation of the method and system illustrates that a Foodie or User may be better off in their blood chemistry by adding ingredients which have a negative correlation, yet positive expected value gain, to blood chemistry because the variance of the blood chemistry has been reduced. To quantify the diversification of various food ingredients we discuss the terms of covariance and correlation. The covariance measures how much the blood chemistry of two ingredients or meals move in tandem. A positive covariance means the ingredients move together with respect to the effects on blood chemistry. A negative covariance means the ingredients move inversely with their effect on blood chemistry. To measure covariance we look at surprises of deviations to blood chemistry in each scenario. In the following implementation of the method and system as stated in 1830 of FIG. 18C, the product will be positive if the blood chemistry of the two ingredients move together across scenarios, such as if both ingredients exceed their expectations on effect on blood chemistry or both ingredients fall short together. If the ingredients effect on blood chemistry move in such a way that when Rapini has a positive effect on blood chemistry and chocolate has a negative effect on blood chemistry, then the product of the equation in 1830 would be negative. Equation 1840 in FIG. 18D is thus a good measure of how the two ingredients move together to affect blood chemistry across all scenarios, which is defined as the covariance.

In an exemplary embodiment in FIG. 19A, an easier statistic to interpret than covariance is the correlation coefficient, which scales the covariance to a value between negative 1 (perfect negative correlation) and positive 1 (perfect positive correlation). The correlation coefficient between two ingredients equals their covariance divided by the product of the standard deviations. In FIG. 19A, using the Greek letter rho, we find in equation 1910 the formula for correlation in an exemplary embodiment. The correlation equation 1910 can be written to solve for covariance or correlation. Studying equation 1910, one may observe that foods which have a perfect correlation term of 1 have their expected value of blood chemistry as just the weighted average of the any two ingredients. If the correlation term in 1910 has a negative value, then the combination of ingredients lowers the standard deviation of the combined ingredients. The mathematics of equations 1910 and 1920 of FIG. 19B show that foods can have offsetting effects which can help overall target blood chemistry readings and health. Combinations of ingredients where the ingredients are not perfectly correlated always offer a better combination to reduce blood chemistry volatility while moving more efficiently toward target ranges.

In an exemplary embodiment in FIG. 19B, the impact of the covariance of individual ingredients on blood chemistry is apparent in the formula in 1920 for blood chemistry variance.

The most fundamental decision of a Foodie is how much of each food should you eat, and how will it affect my health and blood chemistry. Therefore, one implementation of the method and system covers the blood chemistry tradeoff between combinations of ingredients, dishes, various portfolios of ingredients, recipes, meals, prepared dishes, or restaurant entrees.

In an exemplary embodiment in FIG. 19C, recalling the Foodie Score or Utility equation of a user in 1410 of FIG. 14A, the Foodie attempts to maximize his or her utility level or Foodie score by choosing the best allocation of a portfolio of ingredients or menu selection written as the equation in 1930.

Constructing the optimal portfolio of ingredients, recipe, menu, or meal is a complicated statistical task. The principle that the method and system follow is the same used to construct a simple two ingredient recipe or combination in an exemplary scenario. To understand the formula for the variance of a portfolio of ingredients more clearly, we must recall that the covariance of an ingredient with itself is the variance of that ingredient, such as written in FIG. 20A. Wing1 and Wing2 of matrix 2010 are short for the weight associated with ingredient or meal 1 and ingredient or meal 2. The matrix 2010 is simply the bordered covariance matrix of the two ingredients or meals.

In the embodiment of the method and system in FIG. 20B, the descriptive statistics for two ingredients are listed as the expected value and standard deviation, as well as covariance and correlation between the exemplary ingredients. The parameters for the joint probability distribution of returns is shown in matrix 2020 of FIG. 20B.

Figures 21A, 21B:
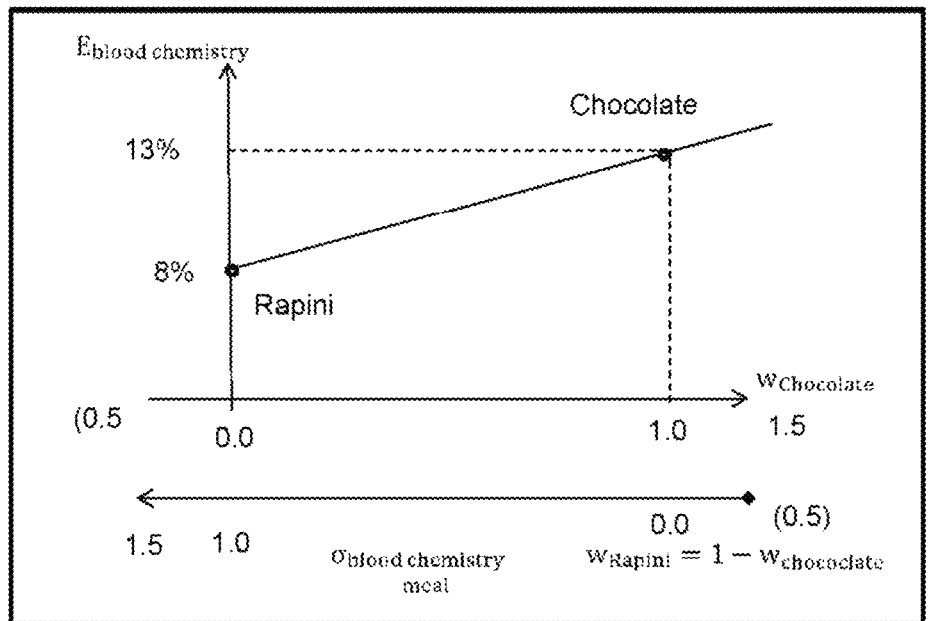
FIGS. 21A and 21B illustrate an exemplary scenario of an experiment with different proportions to observe the effect on the expected blood chemistry and variance of blood chemistry with various weightings.

The embodiments of the method and system in FIG. 21A and FIG. 21B illustrate an exemplary scenario of experiment with different proportions to observe the effect on the expected blood chemistry and variance of blood chemistry. Suppose the proportion of the meal weight of rapini is changed. The effect on the blood chemistry is plotted in FIG. 21A. When the proportion of the meal that is rapini varies from a weight of zero to one, the effect on blood chemistry change toward the target goes from 13% (expected blood chemistry of chocolate) to 8% (expected blood chemistry of rapini). Of course, varying proportions of a meal also has an effect on the standard deviation of blood chemistry. FIG. 21B presents various standard deviation for various weights of rapini and chocolate, as shown in table 2120.

Figure 22A:
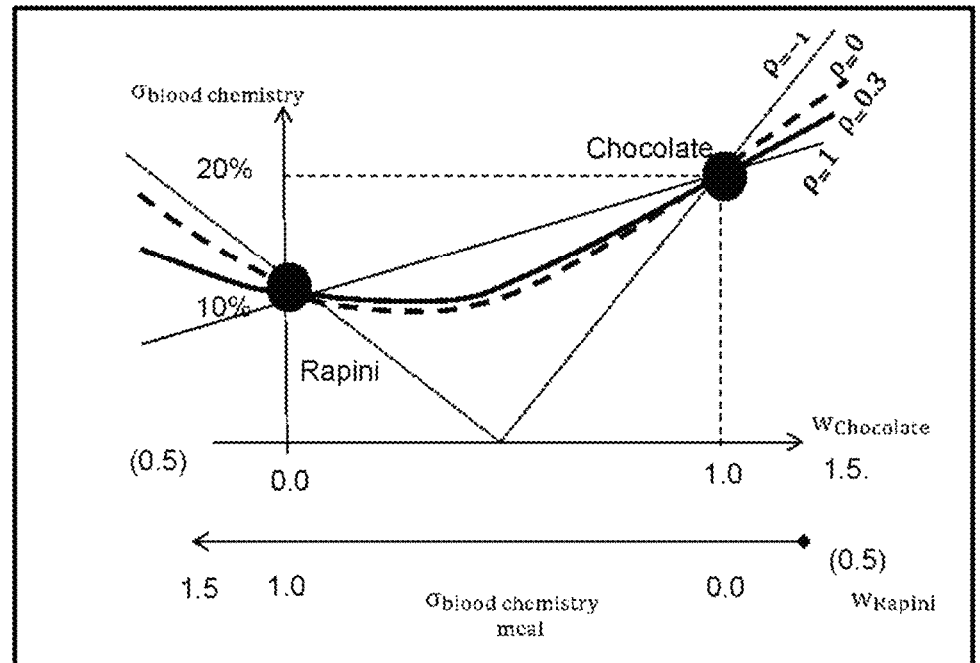
FIGS. 22A and 22B illustrate an exemplary case of the meal combination blood chemistry standard deviation when correlation rho is at 0.30.

In the exemplary case of the meal combination blood chemistry standard deviation, when correlation rho is at 0.30, as shown in FIG. 22A, with the thick curved black line labeled rho=0.3. Note that the combined meal blood chemistry of rapini and chocolate is a minimum variance combination that has a standard deviation smaller than that of either rapini or chocolate as individual ingredients. FIG. 22A highlights the effect of ingredient combinations lowering overall standard deviation. The other three lines in FIG. 22A show how blood chemistry standard deviation varies for other values of the correlation coefficient, holding the variances of the ingredients constant. The dotted curve where rho=0 in FIG. 22A depicts the standard deviation of blood chemistry with uncorrelated ingredients. With the lower correlation between the two ingredients, combination is more effective and blood chemistry standard deviation is lower. We can see that the minimum standard deviation of the meal combination in table 2120 shows a value of 10.29% when rho=0. Finally the upside down triangular broken dotted line represents the potential case where rho=−1 and the ingredients are perfectly negatively correlated. In the rho=−1 case, the solution for the minimum variance combination is a rapini weight of 0.625 and a chocolate weight of 0.375, as shown in FIG. 22A. The method and system can combine FIG. 21A and FIG. 22A to demonstrate the relationship between the ingredients combination's level of standard deviation to blood chemistry and the expected improvement or decline in expected blood chemistry given the ingredient combination parameters as shown in 2220 of FIG. 22B.

Figure 22B:
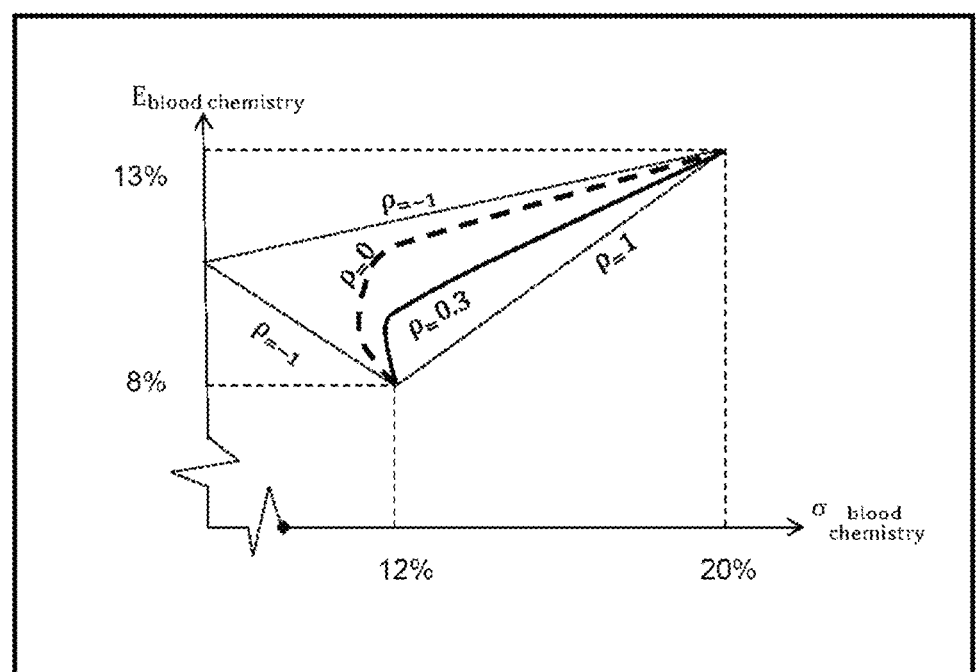

The embodiment illustrated in FIG. 22B shows for any pair of ingredients or meals which may be illustrated for an exemplary case, but not limited to the exemplary case w(chocolate) and w(rapini), the resulting pairs of combinations from 2210, 2120, and 2110 are plotted in 2220. The solid curved line in 2220 labeled with rho=0.3 shows the combination opportunity set while correlation equals 0.3. The name opportunity set is used because it shows the combination of expected blood chemistry and standard deviation of blood chemistry of all combinations that can be constructed from the two available ingredients. The broken dotted lines show the combination opportunity set for the other values of the correlation coefficient. The line farthest to the right, which is the straight line connecting the combinations where the term rho equals one, shows there are no benefits to blood chemistry from combinations between ingredients where the correlation between the two ingredients is perfectly positive or where the term rho equals one. The opportunity set is not "pushed" to the northwest. The curved dotted line to the left of the curved solid line where the term rho equals zero shows that there are greater benefits to blood chemistry when the correlation coefficient between the two ingredients is zero than when the correlation coefficient is positive. Finally the broken line where the term rho equals negative one shows the effect of perfectly negative correlation between ingredients. The combination opportunity set is linear, but offers the perfect offset between ingredients to move toward target blood chemistry. In summary, although the expected blood chemistry of any combination of ingredients is simply the weighted average of the ingredients expected blood chemistry, this is not true for the combination of ingredients standard deviation. Potential benefits from combinations of ingredients arise when correlation is less than perfectly positive. The lower the correlation coefficient, the greater the potential benefit of combinations. In the extreme case of perfect negative correlation between ingredients, the method and system show a perfect offset to blood chemistry and we can construct a zero-variance combination of ingredients.

Suppose the exemplary case where the Foodie wishes to select the optimal combination from the opportunity set. The best combination will depend upon the Foodie's preferences and aversion to the standard deviation of ingredients. Combinations of ingredients to the northeast in FIG. 22B provide higher movements towards expected target blood chemistry, but impose greater levels of volatility of ingredients on blood chemistry. The best trade-off among these choices is a matter of personal preference. Foodies with greater desire to avoid volatility in their blood chemistry will prefer combinations of ingredients in the southwest, with lower expected movement toward target blood chemistry, but lower standard deviation of blood chemistry.

Figures 23A, 23B:
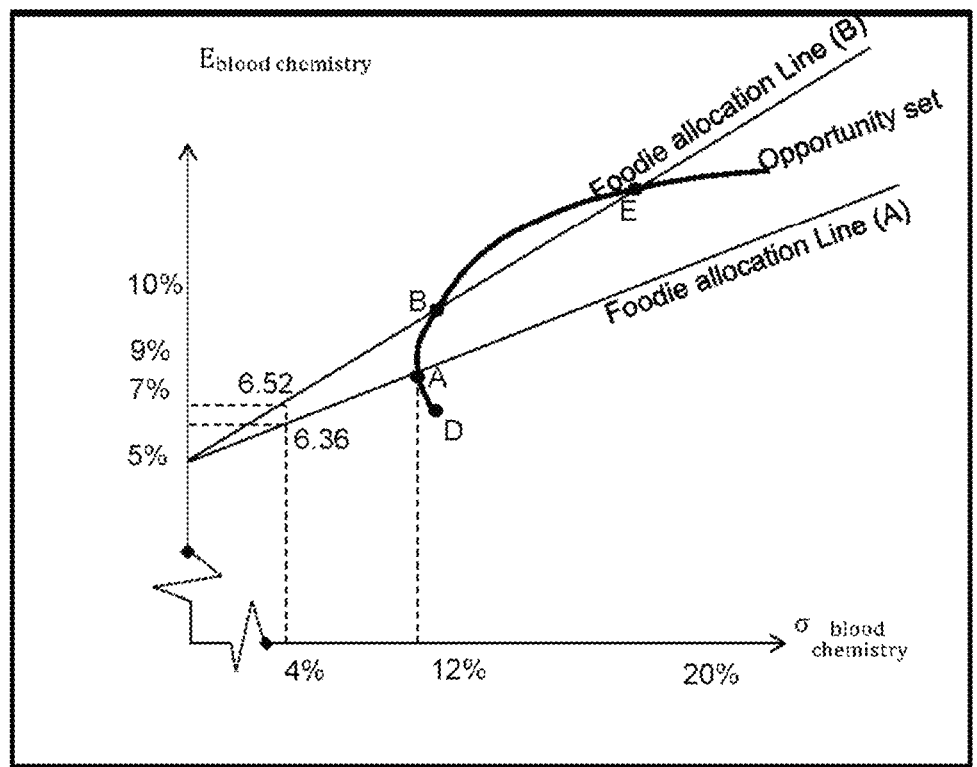
FIGS. 23A and 23B illustrate the opportunity set generated from the joint probability distribution of the combination of ingredients of rapini and chocolate using the data from FIG. 20B as well as the slope of the reward to variability ratio or Foodie allocation line (A).

In the embodiment illustrated in FIG. 22B, most Foodies recognize the really critical decision is how to divvy up their selection amongst ingredients or meal combinations. In the embodiment of the method and system in FIG. 23A, the exemplary diagram is a graphical solution. FIG. 23A shows the opportunity set generated from the joint probability distribution of the combination of ingredients rapini and chocolate using the data from FIG. 21B. Two possible allocation lines are drawn in 2310 of FIG. 23A and labeled "Foodie allocation line". The first Foodie allocation line (A) is drawn through the minimum variance ingredient combination point A, and which is divided as 82% rapini and 18% chocolate. The ingredient combination has an expected target blood chemistry movement of 8.9% and its standard deviation is 11.45% blood chemistry. The reward to variability ratio or slope of the Foodie allocation line combining a zero variance ingredient (which may be certain types of water) with rapini and chocolate with the aforementioned weights of 82% rapini and 18% chocolate, forms an equation listed in FIG. 23B. Accordingly the exemplary slope 2320 of Foodie Allocation Line (A) is 0.34. Considering the embodiment in FIG. 23A of Foodie allocation line (B), the ingredient combination was 70% rapini and 30% chocolate, with the expected movement towards target blood chemistry is 9.5%. Thus the reward to variability ratio or slope of Foodie allocation line(B) is 9.5 minus 5 divided by 11.7, which equals 0.38 or a steeper slope as illustrated in FIG. 23A. If the Foodie allocation line (B) has a better reward to variability ratio than the Foodie allocation line (A), then for any level of standard deviation that a Foodie is willing to bear, the expected target blood chemistry movement is higher with the combination of point B. FIG. 23B illustrates the aforementioned exemplary case, showing that Foodie allocation line (B) intersection with the opportunity set at point B is above the Foodie allocation line (A) intersection with the opportunity set point A. In this case, point B allocation combination dominates point A allocation combination. In fact, the difference between the reward to variability ratio is the difference between the two Foodie allocation line (A) and (B) slopes. The difference between the two Foodie allocation line slopes is 0.38-0.34=0.04. This means that the Foodie gets four extra basis points of expected blood chemistry movement toward the target with Foodie allocation line (B) for each percentage point increase in standard deviation of blood chemistry. If the Foodie is willing to bear a standard deviation of blood chemistry of 4%, the Foodie can achieve a 5.36% (5+4×0.34) expected blood chemistry movement to the target range along Foodie allocation line (A), and, with Foodie allocation line (B), the Foodie can achieve an expected movement of blood chemistry to the target of 6.52% (5+4×0.38). Why stop at point B? The Foodie can continue to ratchet up the Foodie allocation line until it ultimately reaches the point of tangency with the Opportunity set. This aforementioned exemplary scenario in FIG. 23A must yield the Foodie allocation line with the highest feasible reward to variability ratio.

The embodiment illustrated in exemplary scenario FIG. 24A shows the highest sloping Foodie allocation line (C) at point P intersecting with the opportunity set. Point P is the tangency combination of ingredients where the expected blood chemistry target movement is the highest relative to the opportunity set and standard deviation of ingredients or meal combinations, as shown in 2410. The optimal combination or allocation of ingredients is labeled point P. At Point P, the expected blood chemistry movement to the target is 11% while the standard deviation of point P is 14.2%. In practice, we obtain the solution to the method and system with a computer program with instructions to perform the calculations for the Foodie. The method process to obtain the solution to the problem of the optimal mix of ingredients or dish combinations of weight rapini and weight chocolate, or any other combination of ingredients, is the objective of the method and system.

There are many approaches toward optimization which are covered under method and system to optimize blood chemistry through food ingredients which may be utilized for computational efficiency, but the method and system may use as one approach of many approaches where the method finds the weights for various ingredients that result in the highest slope of the Foodie allocation line (C), as shown in 2410. In other words, the method and system may find the weights that result in the variable combination with the highest reward to variability ratio. Therefore the objective function of the method and system may maximize the slope of the Foodie allocation line for any possible combination of ingredients. Thus the objective function of the method and system may show the slope as the ratio of the expected blood chemistry of the combination of ingredients less the blood chemistry of a zero standard deviation blood chemistry ingredient (perhaps water) divided by the standard deviation of the combination of ingredients, as illustrated in FIG. 24B. For the combination of ingredients with just two ingredients, the expected blood chemistry movement toward the target and standard deviation of blood chemistry of the combination of ingredients is illustrated in FIG. 24B. When the method and system maximize the objective function, the slope of the foodie allocation line is subject to the constraint that the combination weights sum to one or one hundred percent, as shown in 2420 of FIG. 24B. In other words the weight of the rapini plus the weight of the chocolate must sum to one. Accordingly, the method and system may solve a mathematical problem formulated as shown in FIG. 25A, which is the standard problem in calculus: maximize the slope of the foodie allocation line subject to the condition that the sum of the weight of all the ingredients will sum to one.

In the embodiment case illustrated in FIG. 25B, the exemplary case may include two ingredients or meal combinations, but the system and method are able to process any amount of ingredients or meal combinations with an extension of the calculus equations of 2510 in FIG. 25A. In the exemplary case of only two ingredients, FIG. 25B illustrates the solution for the weights of the optimal blood chemistry combination of ingredients. Data from 2110, 2120, 2310, 2410, 2420, and 2510 have been substituted in to give the weights of rapini and chocolate in FIG. 25B an exemplary case. The expected blood chemistry has moved 11% toward the target blood chemistry, which incorporates the optimal weights for rapini and chocolate in this exemplary case in 2410, and where the standard deviation is 14.2% in FIG. 24A. The foodie allocation line using the optimal combination in 2510 and 2520 has a slope of 0.42=(11−5)/14.2, which is the reward to variability ratio of blood chemistry. Notice how the slope of the foodie allocation line exceeds the slope of foodie allocation line (B) and foodie allocation line (A) in FIG. 23A, as it must if it is to be the slope of the best feasible foodie allocation line. A foodie with a coefficient term A in FIG. 14A equal to 4 would then make a combination as follows in FIG. 25C. Thus the foodie would select 74.39% of her/his food allocatin in the combination of rapini and chocolate and 25.61% in water or an ingredient which has zero standard deviation to blood chemistry, as shown in 2530 of FIG. 25C. Of the 74.39% of the food ingredient selection, 40% of the 74.39% or (0.4× 0.7439=0.2976) would go to rapini and 60% of 74.39% or (0.60×0.7439=0.4463) would go toward chocolate. The graphical solution of the equations in FIG. 25A, FIG. 25B and FIG. 25C is illustrated in FIG. 26A.

Once the specific two ingredient case has been explained for the method and system, generalizing the embodiment to the case of many ingredients is straightforward. The summarization of steps are outlined in FIG. 26B.

Figure 27A:
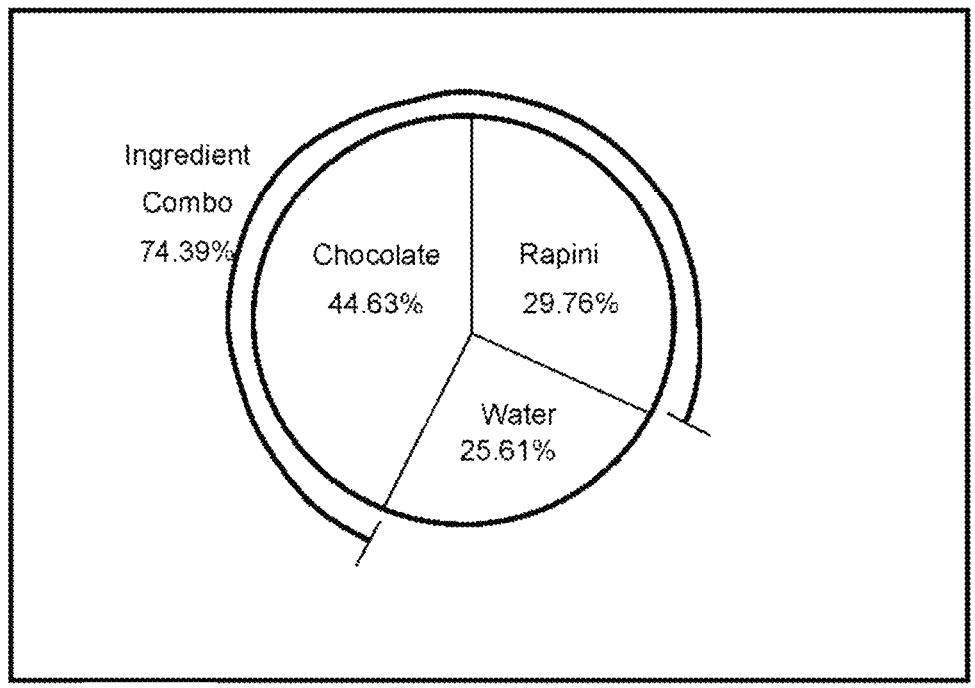
FIGS. 27A and 27B illustrate the graphical solution of the user ingredient allocation method as well as the minimum variance frontier of ingredients which is the graph of the lowest possible ingredient variance combination for a given target food chemistry and its effect on blood chemistry.

The embodiment of FIG. 27A illustrates a combination of ingredients for the optimal combination in the form of a pie chart. Before moving on it is important to understand that the two ingredients described could be meals or combinations of ingredients. Accordingly the method and system may consider the blood chemistry characteristics of single ingredients or combinations of ingredients, which can then form an ingredient as a meal, such as expected blood chemistry, variance and covariance and correlation. Accordingly there can be diversification within ingredients, as some ingredients are combinations of ingredients.

Now we can generalize the two ingredient embodiment of the method and system to the case of many ingredients alongside water or an ingredient with near zero blood chemistry variance or standard deviation. As in the case of the two ingredient embodiment, the problem is solved by the method and system in three parts. First, we identify the expected blood chemistry contribution of the ingredient and standard deviation of that ingredient contribution to blood chemistry. Second, the method and system identifies the optimal combination of ingredients by finding the combination weights that result in the steepest foodie allocation line. Last, the method and system may choose an appropriate complete combination by mixing the combination of water or a zero blood chemistry standard deviation ingredient with the combination of ingredients that carry various standard deviation and correlations. The ingredient opportunities available to the Foodie must be determined in the method and system. These ingredient opportunities are summarized by the minimum variance blood chemistry frontier of ingredients. This frontier is a graph of the lowest possible combination variances that can be attained for a given combination of expected blood chemistry contribution. Given the set of data for expected blood chemistry contribution, variances and covariances of blood chemistry, and expected covariances of blood chemistry of combinations, we can calculate the minimum blood chemistry variance combination for any targeted blood chemistry contribution. Performing such calculations for many such expected blood chemistry combinations results in a pairing between expected blood chemistry contributions and minimum variance blood chemistry contributions that offer the expected blood chemistry contributions. The plot of these expected blood chemistry contribution and standard deviation pairs are presented in FIG. 27B. Notice that all ingredients lie to the right of the frontier. This tells us that combinations that consist only of a single ingredient are inefficient relative to combinations. Adding many ingredients leads to combinations with higher expected blood chemistry contribution and lower standard deviations, shown in 2720 of FIG. 27B. All the combinations in FIG. 27B that lie on the minimum variance frontier from the global minimum variance portfolio and upward provide the best expected blood chemistry contribution and standard deviation of blood chemistry combinations and thus are candidates for the optimal combination. The part of the frontier that lies above the global minimum variance combination is called the efficient frontier. For any combination on the lower portion of the minimum variance frontier, there is a combination with the same standard deviation of blood chemistry but higher expected blood chemistry contribution positioned directly above it. Hence the bottom part of the minimum variance frontier is inefficient.

The second part of the optimization plan involves water or a zero standard deviation blood chemistry ingredient. As before, the method and system search for the foodie allocation line with the highest reward to variability ratio (that is the steepest slope) as shown in FIG. 26A. The foodie allocation line that is supported by the optimal combination point P, is, as before, the combination that is tangent to the efficient frontier. This foodie allocation line dominates all alternative feasible lines. Therefore, combination P in FIG. 26A is the optimal ingredient combination.

Finally, for the last part of the embodiment of the method and system, the Foodie choses the appropriate mix between the optimal ingredient combination and a zero blood chemistry variance ingredient which may include water. In FIG. 26A, the point where Foodie allocation line (C) has a zero standard deviation value is where the expected blood chemistry target movement is 5% or point F.

Now let us consider in the method and system each part of the combination construction problem in more detail. In the first part of the Foodie problem, the analysis of the expected blood chemistry of the ingredient, the Foodie needs, as inputs, a set of estimates of expected blood chemistry target movement for each ingredient and a set of estimates for the covariance matrix, which the method and system provide for the Foodie through the system application.

Suppose that the time period of the analysis for the combination of ingredients between blood and saliva tests was one year. Therefore all calculations and estimates pertain to a one year plan under the method and system. The database system contains the variable n ingredients, where n could be any amount of ingredients. As of now, time zero, we observed the expected blood chemistry of the ingredients such that each ingredient is given the variable label i and an index number of n at time zero. Then the system and method determine how the ingredient affects the Foodie's blood chemistry at the end of one year or time equal to one year. The covariances of the ingredients effects on blood chemistry are usually estimated from historical data for both the Foodie and from Foodie users in the database with similar characteristics. Through the method and system, the Foodie is now armed with the n estimates of the expected effect on blood chemistry of each ingredient and then the n×n estimates in the covariance matrix, in which the n diagonal elements are estimates of the variances of each ingredient. The n squared minus n equals n multiplied by the quantity of n minus 1 off diagonal elements are the estimates of the covariances between each pair of ingredient blood chemistries. We know that each covariance appears twice in the aforementioned table, so actually we have $n(n-1)/2$ different covariance estimates. If the Foodie user considers 50 ingredients or meal combinations, the method and system need to provide 50 estimates of expected blood chemistry results for each respective ingredient or meal combination and $(50\times 49)/2=1,225$ estimates of covariances, which is a daunting task without the assistance of the method and system computer application program. Once these estimates are compiled by the method and system, the expected blood chemistry and variance of any combination of ingredients with weights for any of the respective ingredients can be calculated by the general formulas in FIG. 28A.

Figure 27B:
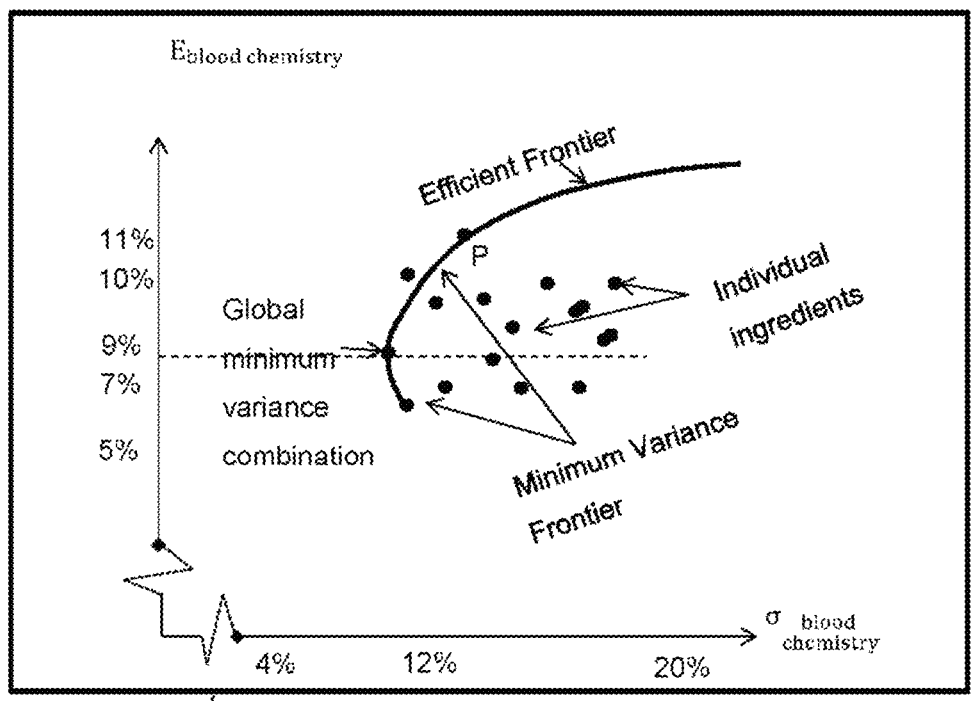
Figures 28A, 28B:
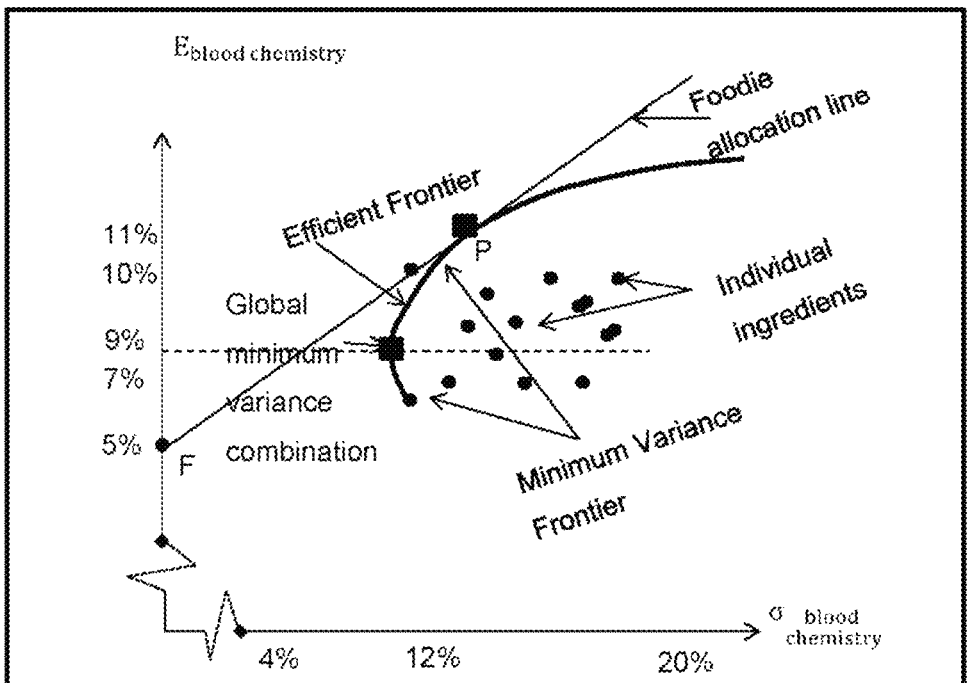
FIGS. 28A and 28B illustrate the expected movement of a users blood chemistry from the ingredient combination as well as the expected variance of blood chemistry.

The general embodiment of an exemplary case of the method and system in FIG. 28A states the expected blood chemistry toward the target blood chemistry of each ingredient and the variance of the blood chemistry of each ingredient, such that the weights of each ingredient can be calculated, as shown in 2810. While many people say "eat a wide variety of food" or "eat a balanced diet" or "don't put all your eggs in one basket", no method or system has attempted to accurately quantify these statements in such a way that mathematics and science can be used to easily make a map for eating. The system and method have coined the phrase, as GPS is to driving, Foodie Body or the blood and saliva to food algorithms are to eating. No longer will Foodies or users guess at how nutrition is affecting their blood and overall health, as math and science will map their progress with a quantitative method and system. The principle behind the method and system is that a Foodie can quantify the set of ingredient combinations that give the highest blood chemistry result to maximize human health and productivity. Alternatively, the efficient frontier in FIG. 27B is the set of ingredient combinations that minimize the variance of blood chemistry for any target blood chemistry. The result is the most efficient method empirically and quantitatively to consume food for human health.

The points marked by rectangles in the exemplary embodiment in FIG. 28B are the result of variance—minimization calculations in the method and system. First we draw the constraint: that is, a horizontal line at the level of required expected blood chemistry target. We then look for the combination of ingredients (point P) with the lowest standard deviation that plots on the Foodie allocation line, as shown in 2820. We then discard the bottom of the minimum variance frontier below the global minimum variance combination as it is inefficient and points above the global minimum variance combination have higher blood chemistry contribution to the target, but a similar standard deviation. Restating the solution that the method and system has completed thus far, the estimate generated by the Foodie utilizing the method and system transforms ingredients and ingredient combinations into a set of expected blood chemistry statistics toward the user's blood chemistry and a covariance matrix of how the ingredients are correlated. This group of estimates shall be called the input list. This input list is then fed into the optimization system and method. Before we proceed to the second step of choosing the optimal combination of ingredients for blood or saliva chemistry, some Foodies may have additional constraints. For example, many Foodies have allergies which preclude certain food ingredient types. The list of potential constraints is large and the method and system allows for the addition of constraints in the optimization method and system. Foodie users of the system and method may tailor the efficient set of ingredients to conform to any desire of the Foodie. Of course, each constraint carries a price tag in the sense that an efficient frontier constructed subject to extra constraints may offer a reward to variability ratio inferior to that of a less constrained set. The Foodie is made aware of this cost through the system and method application and should carefully consider constraints that are not mandated by law or allergies.

Proceeding to step two in the method and system, this step introduces water or a zero variance blood chemistry ingredient that has positive blood chemistry attributes. As before, we ratchet up the Foodie allocation line by selecting different combinations of ingredients until combination P is reached, which is the tangency point of a line from point F to the efficient frontier. Ingredient combination P maximizes the reward to variability ratio, the slope of the Foodie allocation line from point F to combinations on the efficient frontier set.

The method and system embodiment of the general exemplary case may be written in one form as in FIG. 29. Vectors are used to capture variable d inputs or as many inputs as are required to weight in FIG. 29. The method and system may use other techniques to express combination blood and saliva expected target chemistry and variances, but it is convenient to handle large combinations of ingredients in matrix form in FIG. 29.

Figure 30:
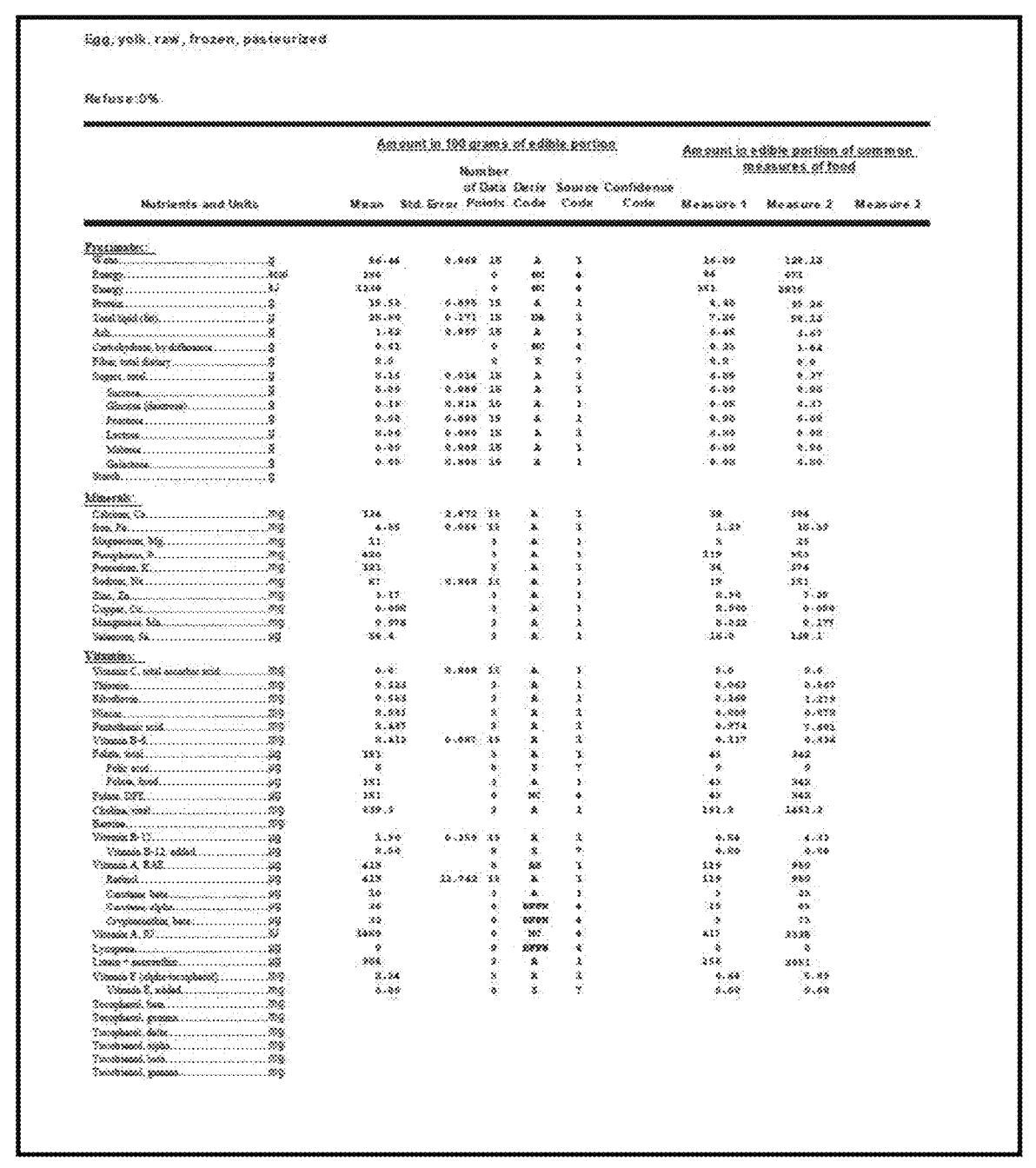
Figure 31:
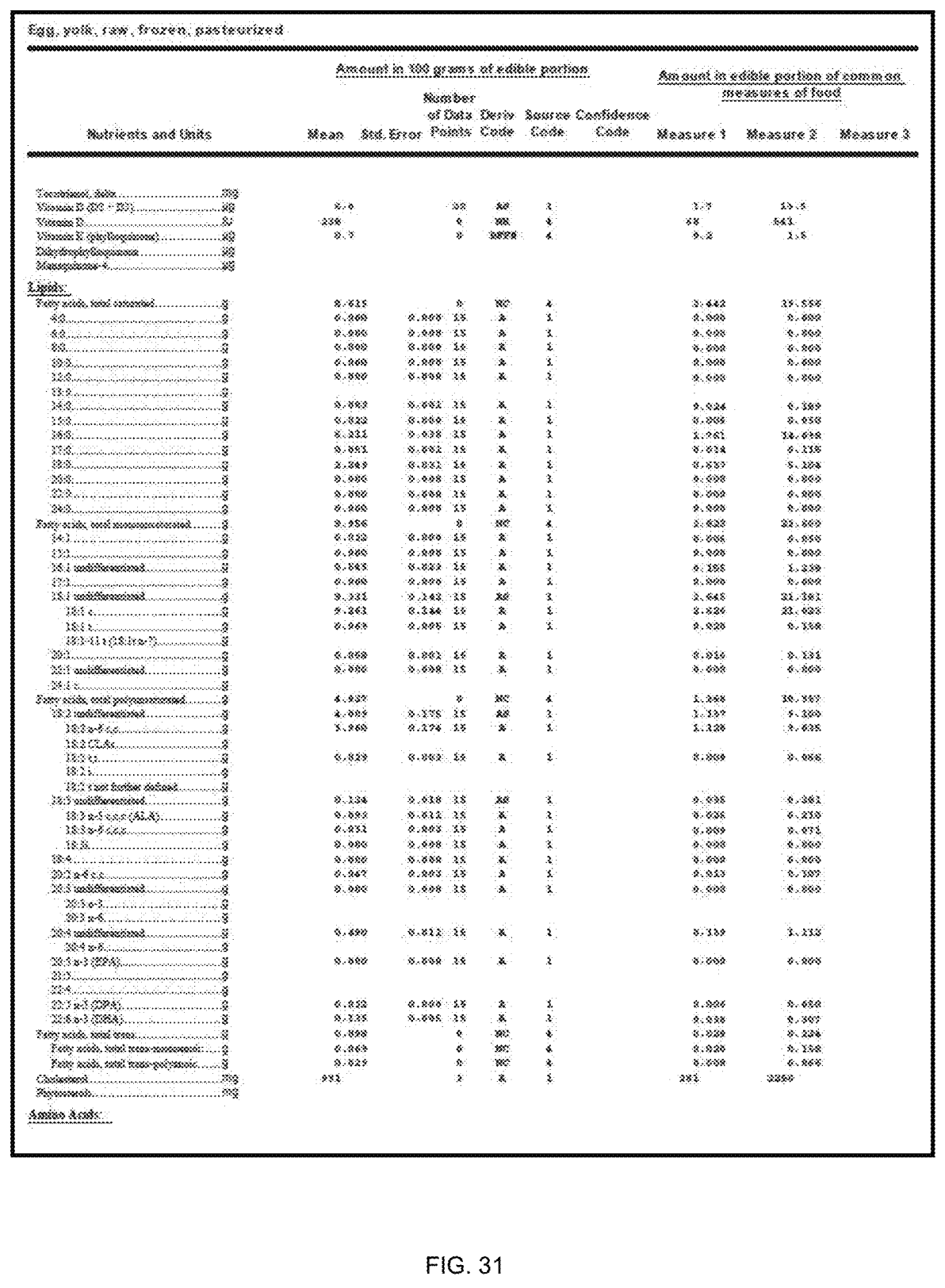
Figure 32:
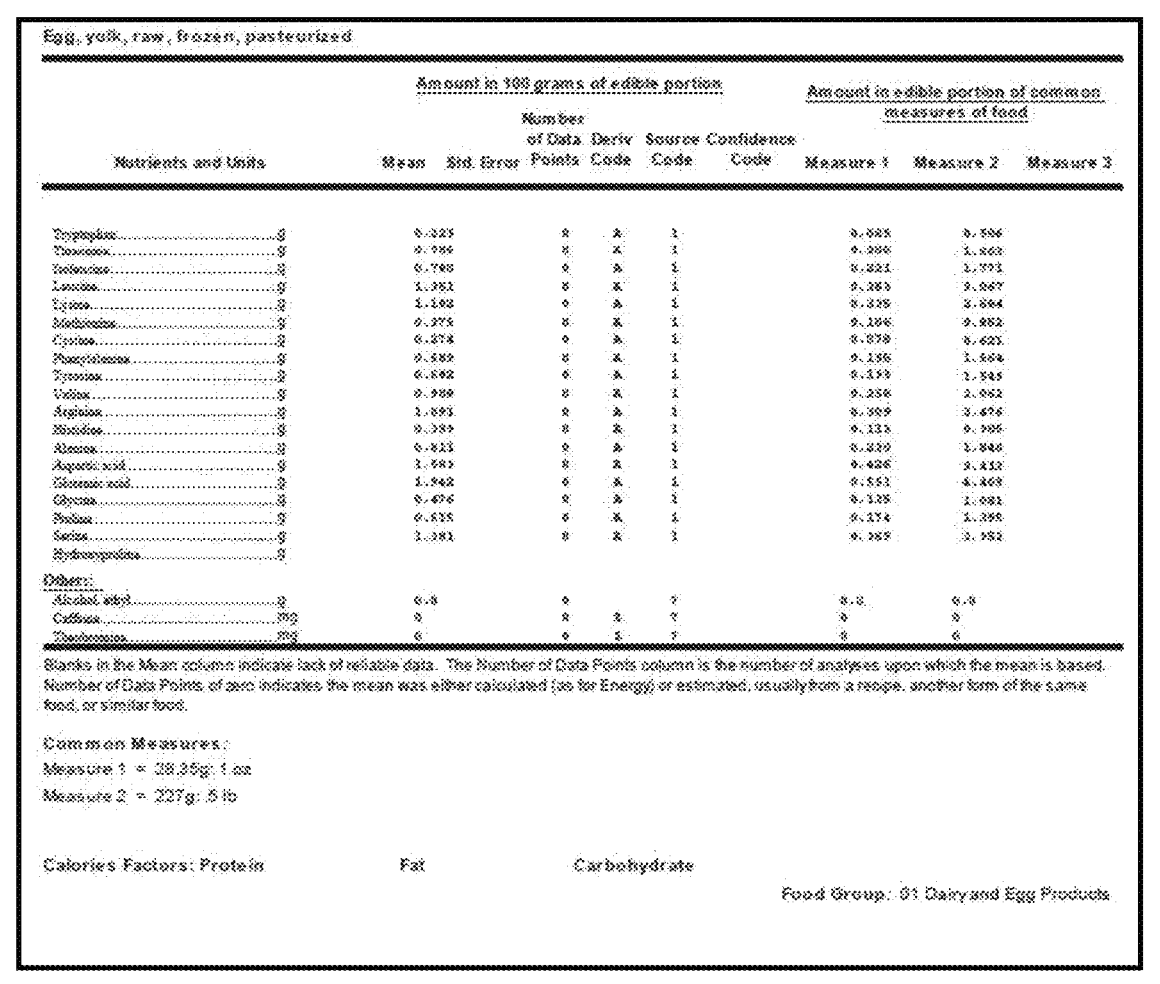

The method and system embodiment in FIG. 30, FIG. 31 and FIG. 32 illustrate one exemplary entry in the system database which measures the nutrition content and standard deviation toward blood and saliva chemistry for egg, yolk, raw, frozen or pasteurized. The method and system database for food 160 may have a mixture of United States Department of Agriculture data and proprietary food data that has higher degrees of differentiation in nutrition levels.

Figure 33:
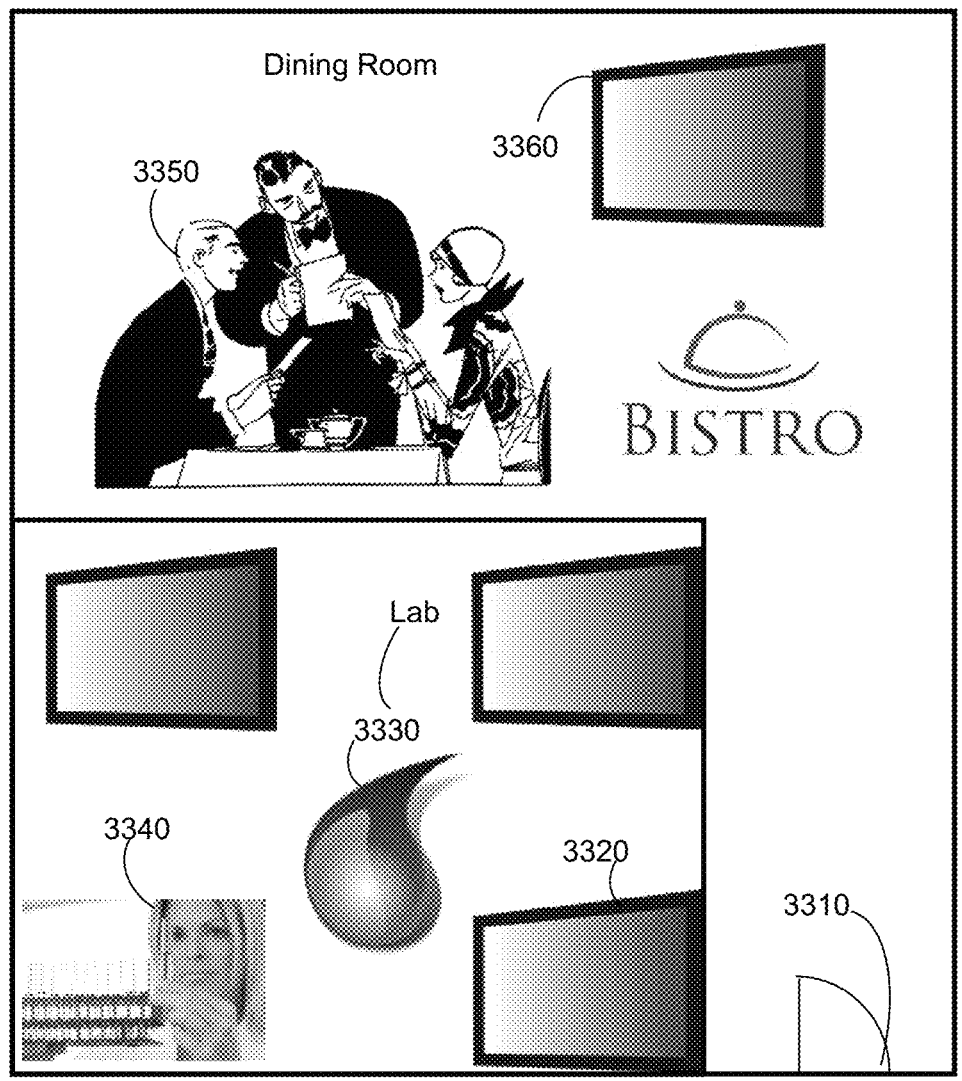
FIG. 33 illustrates a specific education center food establishment where both blood work and a restaurant that has the ability utilize the equations of the methods and teach the users how blood and food interact in the method embodiment.

The method and system embodiment illustrated in FIG. 33 may be one of many distribution and education channels where a retail concept store combines a food database laboratory and a dining experience for the foodie or user. A Foodie may walk into the door 3310 of the retail experience and be given an opportunity to move into the blood laboratory 3330 where they will be given appetizers in a high tech learning center blood lab 3330. Monitor screens or projection devices, both in 2D and 3D, and mixed reality or augmented reality may project visualizations of blood chemistry interactions with food chemistry 3320. After the lab technician secures a blood and saliva sample from the foodie 3340, the user may go into the dining room 3350. In the dining room of the concept retail experience 3350, Foodie experts will assist Foodies with menu selection of blood and saliva optimized food 3360. While FIG. 33 illustrates a retail concept store for the method and system, the method and system may have many outlets such as any grocery store, restaurant, or food distribution point.

Figure 34:
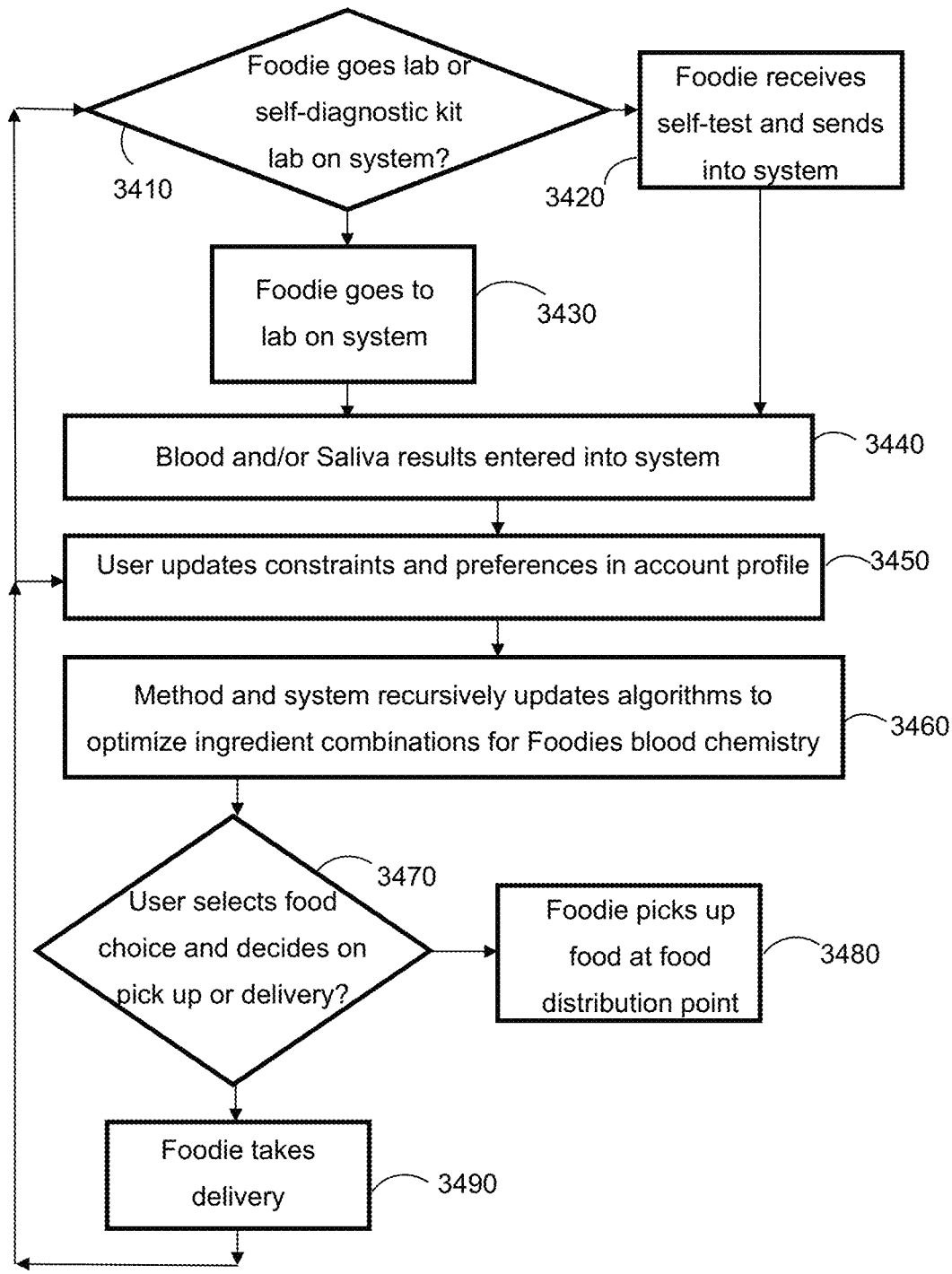
FIG. 34 illustrates an embodiment of one potential flow chart of the method and system processes.

The flow chart illustrated in FIG. 34 for an exemplary scenario of the method and system, a Foodie goes to a lab or orders a self-diagnostic kit 3410. Depending on the Foodies decision 3410 the Foodie either sends in self-test to system 3420 or the lab sends in the results to the system 3430. The blood and/or saliva samples are then entered into the blood and saliva database 3440. The user or Foodie interacts with the system and method to update or select constraints and preferences in their account profile on the system 3450. The method and system recursively updates the algorithm weights and selection combination ingredients based on the optimization program from the system and method based on the foodies blood and saliva chemistry 3460. The Foodie or user then selects either pick up at a food distribution point (grocery store, convenience store, restaurant or other food distribution point) or selects delivery to a point the user desires 3470. The user or foodie may take delivery 3490 or pick up the food at a food distribution point 3480.

The aforementioned description, for purpose of explanation, has been described with reference to specific embodiments. However the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A method, comprising:
   receiving, over one or more wired or wireless networks, consumption data from one or more user interfaces associated with a user, wherein the consumption data comprises data corresponding to a plurality of food ingredients consumed by the user;
   obtaining, over the one or more wired or wireless networks, one or more biological samples data from the user after the plurality of food ingredients have been consumed by the user;
   storing the one or more biological samples data on a first server;
   determining, by one or more computer processing units electronically coupled to the first server, biomarker data for the user based on the one or more biological samples data, wherein the biomarker data comprises data corresponding to one or more measurement levels of one or more biomarkers for the user;
   determining, by the one or more computer processing units, a plurality of expected blood chemistry values of the plurality of food ingredients for the user based on the consumption data and the biomarker data;
   determining, by the one or more computer processing units, a plurality of standard deviation values of the plurality of food ingredients for the user based on the consumption data, the biomarker data, and the plurality of expected blood chemistry values;
   determining, by the one or more computer processing units, a plurality of food combinations based on the plurality of food ingredients, wherein a respective food combination comprises two or more food ingredients of the plurality of food ingredients;
   training a neural network to determine a plurality of optimized weight values for the respective food combination for the user based on the plurality of expected blood chemistry values and the plurality of standard deviation values, wherein the optimized weight values correspond to neural network probability weightings with iterative feedback from the one or more biological samples data;

determining, by the one or more computer processing units, a plurality of optimized food combinations based on the plurality of optimized weight values, wherein the plurality of optimized food combinations is a subset of the plurality of food combinations; and receiving, by one or more user interfaces associated with user over the one or more wired or wireless networks, selection data from the user, wherein the selection data comprises data corresponding to a selection by the user of one or more selected food combinations from the plurality of optimized food combinations.

2. The method of claim 1, wherein the one or more biological samples data comprise one or more blood samples data, one or more saliva samples data, or combinations thereof; and further comprising:

providing, by the one or more computer processing units, the one or more selected food combinations to the user using one or more drones, one or more autonomous vehicles, or combinations thereof.

3. The method of claim 1, wherein determining the plurality of expected blood chemistry values comprises:

determining a plurality of return values of the plurality of food ingredients for the user based on the consumption data and the biomarker data, wherein a respective return value of a respective food ingredient corresponds to an increase or a decrease of the one or more measurement levels towards a target range after the respective food ingredient has been consumed by the user;

determining a plurality of probability weight values for the plurality of return values based on the consumption data and the biomarker data; and determining the plurality of expected blood chemistry values based on the plurality of return values and the plurality of probability weight values.

4. The method of claim 3, wherein determining the plurality of standard deviation values comprises determining the plurality of standard deviation values based on the plurality of expected blood chemistry values, the plurality of return values, and the plurality of probability weight values.

5. The method of claim 1, wherein the respective food combination comprises a dish, a meal, a food product, or combinations thereof.

6. The method of claim 1, wherein the one or more measurement levels of the one or more biomarkers comprise one or more measurement levels for complete blood count, red blood cell, white blood cell, platelets, hemoglobin, hematocrit, mean corpuscular volume, blood chemistry tests, basic metabolic panel, blood glucose, calcium, electrolytes, kidneys, blood enzyme test, troponin, creatine kinase, cholesterol, LDL cholesterol, HDL cholesterol, triglyceride, lipoprotein panel, coagulation panel, or combinations thereof.

7. The method of claim 1, wherein determining the plurality of food combinations comprises:

receiving nutritional data corresponding to the plurality of food ingredients; and determining the plurality of food combinations based on the nutritional data.

8. The method of claim 1, wherein determining the plurality of food combinations comprises:

receiving constraint data from the user, wherein the constraint data comprises data corresponding to one or more dietary preferences of the user;

determining a plurality of constrained ingredients based on the constraint data, wherein the plurality of constrained ingredient comprises at least a subset of the plurality of food ingredients; and determining the plurality of food combinations based on the plurality of constrained ingredients, wherein the respective food combination comprises two or more constrained ingredients of the plurality of constrained ingredients.

9. The method of claim 1, wherein the respective optimized weight value further corresponds to a serving proportion for the respective food ingredient of the respective food combination, wherein the serving proportion comprises a serving size proportion for the respective food ingredient, a calorie count proportion for the respective food ingredient, or combinations thereof.

10. The method of claim 1, wherein a sum of the plurality of optimized weight values for the respective food combination is equal to one.

11. The method of claim 1, wherein determining the plurality of optimized weight values comprises:

determining a plurality of candidate weight values for the respective food combination;

determining a plurality of combined expected values for the respective food combination for the user based on the plurality of candidate weight values and the plurality of expected blood chemistry values;

determining a plurality of covariance values for the plurality of food combinations based on the plurality of expected blood chemistry values, the biomarker data, and the consumption data, wherein a respective covariance value corresponds to the respective food combination;

determining a plurality of combined standard deviation values for the respective food combination based on the plurality of candidate weight values, the plurality of standard deviation values of the plurality of food ingredients, and the respective covariance value; and determining the plurality of optimized weight values for the respective food combination based on the plurality of combined expected values and the plurality of combined standard deviation values.

12. The method of claim 11, wherein determining the plurality of optimized weight values for the respective food combination based on the plurality of combined expected values and the plurality of combined standard deviation values comprises:

determining an opportunity set for the respective food combination based on the plurality of combined expected values and the plurality of combined standard deviation values;

determining one or more allocation lines based on the opportunity set; and determining the plurality of optimized weight values for the respective food combination based on the one or more allocation lines.

13. The method of claim 12, wherein:

determining the one or more allocation lines comprises determining a tangent line corresponding to the opportunity set; and determining the plurality of optimized weight values for the respective food combination based on the one or more allocation lines comprises determining the plurality of optimized weight values for the respective food combination based on the tangent line and the opportunity set.

14. The method of claim 12, wherein determining the plurality of optimized weight values for the respective food combination based on the one or more allocation lines comprises:
determining one or more slope values for the one or more allocation lines based on the plurality of combined expected values, the plurality of combined standard deviation values, and an expected blood chemistry value of a zero standard deviation value food ingredient;
determining a maximum slope value of the one or more slope values; and
determining the plurality of optimized weight values for the respective food combination based on the maximum slope value, the plurality of expected blood chemistry values, the plurality of standard deviation values of the plurality of food ingredients, and the respective covariance value.

15. The method of claim 1, wherein determining the plurality of optimized food combinations comprises:
determining a plurality of utility values for the plurality of food combinations based on the plurality of optimized weight values and one or more utility functions, wherein the one or more utility functions correspond to one or more user preferences of the user; and
determining the plurality of optimized food combinations based on the plurality of utility values.

16. The method of claim 1, further comprising generating a display of the plurality of optimized food combinations for the user.

17. A method, comprising:
receiving, over one or more wired or wireless networks, consumption data from one or more user interfaces associated with a user, wherein the consumption data comprises data corresponding to a plurality of food ingredients consumed by the user;
obtaining, over the one or more wired or wireless networks, one or more biological samples data from the user after the plurality of food ingredients have been consumed by the user;
storing the one or more biological samples data on a first server;
determining, by one or more computer processing units electronically coupled to the first server, biomarker data for the user from the one or more biological samples data, wherein the biomarker data comprises data corresponding to one or more measurement levels of one or more biomarkers for the user;
determining, by the one or more computer processing units, a plurality of expected blood chemistry values of the plurality of food ingredients for the user based on the consumption data and the biomarker data;
determining, by the one or more computer processing units, a plurality of standard deviation values of the plurality of food ingredients for the user based on the consumption data, the biomarker data, and the plurality of expected blood chemistry values;
determining, by the one or more computer processing units, a plurality of food combinations based on the plurality of food ingredients, wherein a respective food combination comprises two or more food ingredients of the plurality of food ingredients;
generating a neural network to determine a plurality of optimized weight values for the respective food combination for the user based on the plurality of expected blood chemistry values and the plurality of standard deviation values, wherein a respective optimized weight value corresponds at least partially to a neural network weighting of a respective food ingredient of the respective food combination or a serving proportion for the respective food ingredient of the respective food combination;
determining, by the one or more computer processing units, a plurality of optimized food combinations based on the plurality of optimized weight values, wherein the plurality of optimized food combinations is a subset of the plurality of food combinations; and
receiving, by one or more user interfaces associated with user over the one or more wired or wireless networks, selection data from the user, wherein the selection data comprises data corresponding to a selection by the user of one or more selected food combinations from the plurality of optimized food combinations.

18. The method of claim 17, further comprising:
providing, by the one or more computer processing units, the one or more selected food combinations to the user using one or more drones, one or more autonomous vehicles, or combinations thereof; and
wherein determining the plurality of optimized weight values comprises:
determining a plurality of candidate weight values for the respective food combination;
determining a plurality of combined expected values for the respective food combination for the user based on the plurality of candidate weight values and the plurality of expected blood chemistry values;
determining a plurality of covariance values for the plurality of food combinations based on the plurality of expected blood chemistry values, the biomarker data, and the consumption data, wherein a respective covariance value corresponds to the respective food combination;
determining a plurality of combined standard deviation values for the respective food combination based on the plurality of candidate weight values, the plurality of standard deviation values of the plurality of food ingredients, and the respective covariance value; and
determining the plurality of optimized weight values for the respective food combination based on the plurality of combined expected values and the plurality of combined standard deviation values.

* * * * *